(12) United States Patent  (10) Patent No.: US 8,761,890 B2
Gupta et al.  (45) Date of Patent:  Jun. 24, 2014

(54) ELECTRICAL STIMULATION PROGRAMMING

(71) Applicant: Medtronic, Inc., Minneapolis, MN (US)

(72) Inventors: Rahul Gupta, St. Louis Park, MN (US); Steven M. Goetz, North Oaks, MN (US); Maciej T. Lazarewicz, Maple Grove, MN (US); Gabriela C. Molnar, Fridley, MN (US); Dwight E. Nelson, Shoreview, MN (US); Jianping Wu, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/748,633

(22) Filed: Jan. 24, 2013

(65) Prior Publication Data

US 2013/0268019 A1   Oct. 10, 2013

Related U.S. Application Data

(60) Provisional application No. 61/622,505, filed on Apr. 10, 2012, provisional application No. 61/639,606, filed on Apr. 27, 2012.

(51) Int. Cl.
*A61N 1/36* (2006.01)
(52) U.S. Cl.
USPC .......................................................... 607/45
(58) Field of Classification Search
USPC .......................................................... 607/45
See application file for complete search history.

(56) References Cited

U.S. PATENT DOCUMENTS

| | | | |
|---|---|---|---|
| 5,713,922 A * | 2/1998 | King | 607/2 |
| 6,587,724 B2 | 7/2003 | Mann | |
| 6,622,048 B1 | 9/2003 | Mann et al. | |
| 7,082,333 B1 | 7/2006 | Bauhahn et al. | |
| 7,216,000 B2 | 5/2007 | Sieracki et al. | |
| 7,346,382 B2 * | 3/2008 | McIntyre et al. | 600/407 |
| 7,386,348 B2 | 6/2008 | North et al. | |
| 7,561,918 B2 | 7/2009 | Armstrong et al. | |
| 7,620,456 B2 | 11/2009 | Gliner et al. | |
| 7,933,655 B2 | 4/2011 | Sieracki et al. | |
| 2005/0070781 A1 | 3/2005 | Dawant et al. | |
| 2006/0017749 A1 | 1/2006 | McIntyre et al. | |
| 2006/0241720 A1 | 10/2006 | Woods et al. | |
| 2007/0083104 A1 | 4/2007 | Butson et al. | |
| 2009/0287271 A1 | 11/2009 | Blum et al. | |
| 2011/0066407 A1 | 3/2011 | Butson et al. | |
| 2012/0271189 A1 | 10/2012 | Nelson et al. | |

OTHER PUBLICATIONS

Chaturvedi, et al., "Subthalamic Nucleus Deep Brain Stimulation: Accurate Axonal Threshold Prediction with Diffusion Tensor Based Electronic Field Models," Aug. 30, 2006.
Butson et al., "Patient-specific analysis of the volume of tissue activated during deep brain stimulation," Dec. 2, 2006, 10 pp.
International Search Report and Written Opinion from International Application No. PCT/US2013/023058, dated May 14, 2013, 16 pp.

* cited by examiner

*Primary Examiner* — George Manuel
(74) *Attorney, Agent, or Firm* — Shumaker & Sieffert, P.A.

(57) ABSTRACT

In one example, the disclosure relates to a method comprising receiving at least one electrical stimulation parameter value defining electrical stimulation for delivery via one or more electrodes to a tissue site, and determining, via one or more processors, a volume of sub-activation threshold impact for tissue from the delivery of the electrical stimulation to the tissue site.

25 Claims, 13 Drawing Sheets

ELECTRICAL STIMULATION PROGRAMMING

RELATED APPLICATIONS

This application claims priority to commonly-assigned provisionally-filed patent applications 61/622,505 filed Apr. 10, 2012, and 61/639,606 filed Apr. 27, 2012, both of which are incorporated herein by reference in their entireties.

TECHNICAL FIELD

The disclosure relates to medical devices and, more particularly, to medical devices that deliver electrical stimulation therapy.

BACKGROUND

Medical devices may be used to treat a variety of medical conditions. Medical electrical stimulation devices, for example, may deliver electrical stimulation therapy to a patient via implanted electrodes. Electrical stimulation therapy may include stimulation of nerve, muscle, brain tissue or other tissue within a patient. An electrical stimulation device may be fully implanted within the patient. For example, an electrical stimulation device may include an implantable electrical stimulation generator and one or more implantable leads carrying electrodes. Alternatively, the electrical stimulation device may comprise a leadless stimulator. In some cases, implantable electrodes may be coupled to an external electrical stimulation generator via one or more percutaneous leads or fully implanted leads.

Patients afflicted with movement disorders or other neurodegenerative impairment, whether by disease or trauma, may experience muscle control and movement problems, such as rigidity, bradykinesia (i.e., slow physical movement), rhythmic hyperkinesia (e.g., tremor), nonrhythmic hyperkinesia (e.g., tics) or akinesia (i.e., a loss of physical movement). Movement disorders may be found in patients with Parkinson's disease, multiple sclerosis, and cerebral palsy, among other conditions. Delivery of electrical stimulation and/or a fluid (e.g., a pharmaceutical drug) by a medical device to one or more sites in a patient, such as a brain, spinal cord, leg muscle or arm muscle, in a patient may help alleviate, and in some cases, eliminate symptoms associated with movement disorders.

SUMMARY

In general, the disclosure relates to systems, devices, and techniques for determining a volume of sub-activation threshold impact (VSTI) for tissue, and utilizing the VSTI for programming of a medical device configured to deliver electrical stimulation to patient. The VSTI for tissue may be determined for electrical stimulation delivered to the tissue site via one or more electrodes of a medical device, such as an implantable medical device (IMD), according to one or more stimulation parameters. VSTI may refer to the volume of tissue electrically influenced by the delivery of stimulation via one or more electrodes to a tissue site, but in which neurons are not activated by the electrical stimulation, e.g., the neurons do not fire action potentials in response to the stimulation. For example, the VSTI may refer to the volume of tissue that, while not activated, is electrically influenced in a manner that disrupts pathological activity of the brain as a result of the stimulation delivered to a tissue site, e.g., within the brain. Such stimulation may treat or otherwise manage a patient disorder by disrupting pathological brain activity. In some examples, while neurons within the VSTI may not be activated, neurons of the tissue within the VSTI may be desynchronized or synchronized by electrical stimulation below an activation threshold.

In one example, the disclosure is directed to a method comprising receiving at least one electrical stimulation parameter value defining electrical stimulation for delivery via one or more electrodes to a tissue site; and determining, via one or more processors, a volume of sub-activation threshold impact from the delivery of the electrical stimulation to the tissue site.

In another example, the disclosure is directed to systems one or more processors configured to receive at least one electrical stimulation parameter value defining electrical stimulation for delivery via one or more electrodes to a tissue site, and determine a volume of sub-activation threshold impact from the delivery of the electrical stimulation to the tissue site.

In another example, the disclosure is directed to a medical device system comprising means for receiving at least one electrical stimulation parameter value defining electrical stimulation for delivery via one or more electrodes to a tissue site; and means for determining a volume of sub-activation threshold impact from the delivery of the electrical stimulation to the tissue site.

In another example, the disclosure relates to a non-transitory computer-readable storage medium comprising instructions to cause one or more processors to receive at least one electrical stimulation parameter value defining electrical stimulation for delivery via one or more electrodes to a tissue site; and determine a volume of sub-activation threshold impact from the delivery of the electrical stimulation to the tissue site.

In another example, the disclosure relates to a computer-readable storage medium comprising instructions. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, random access memory or RAM) or any other type of volatile or non-volatile memory that stores instructions (e.g., in the form of a computer program or other executable) to cause a programmable processor to perform one or more of the techniques described herein.

The details of one or more aspects of the disclosure are set forth in the accompanying drawings and the description below. Other features, objects, and advantages will be apparent from the description and drawings, and from the claims.

DETAILED DESCRIPTION

Figure 1:
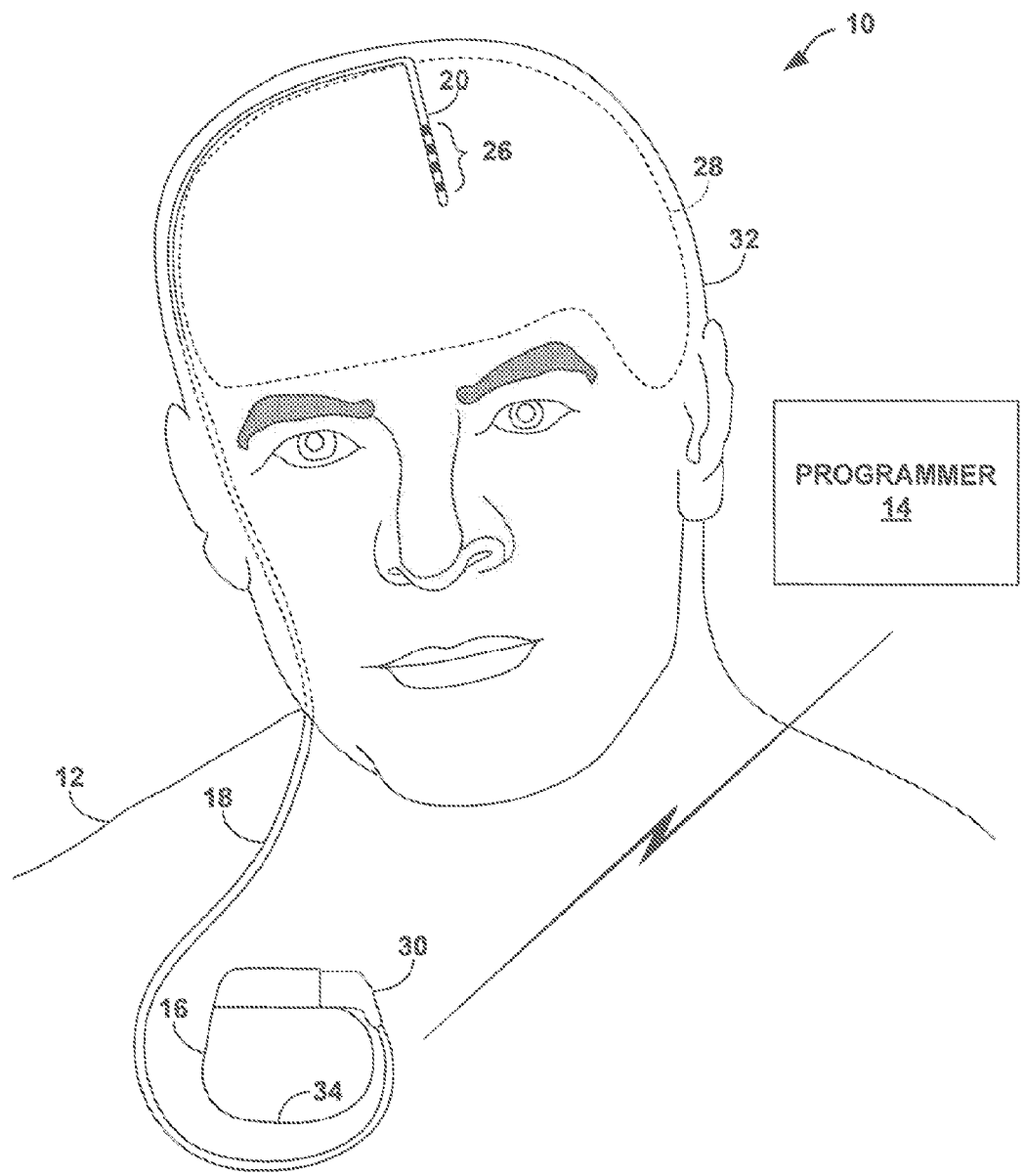
FIG. 1 is a conceptual diagram illustrating an example therapy delivery system.

As described above, the disclosure relates to systems, devices, and techniques for determining a VSTI for tissue, and utilizing the VSTI for programming of a medical device configured to deliver electrical stimulation to patient. The VSTI for tissue may be determined for electrical stimulation delivered to the tissue site via one or more electrodes of a medical device, such as an implantable medical device (IMD), according to one or more stimulation parameters. VSTI may refer to the volume of tissue electrically influenced by the delivery of stimulation via one or more electrodes to a tissue site, but in which neurons are not activated by the electrical stimulation, e.g., the neurons do not fire action potentials in response to the stimulation. For example, the VSTI may refer to the volume of tissue that, while not activated, is electrically influenced in a manner that disrupts pathological activity of the brain as a result of the stimulation delivered to a tissue site, e.g., within the brain. Such stimulation may treat or otherwise manage a patient disorder by disrupting pathological brain activity. In some examples, while neurons within the VSTI may not be activated, neurons of the tissue within the VSTI may be desynchronized or synchronized by electrical stimulation below an activation threshold.

The delivery of electrical stimulation therapy may provide relief to a patient from many conditions. However, the efficacy of the stimulation therapy may be contingent on a clinician correctly positioning one or more stimulation electrodes and programming the stimulation parameters in a manner that provides therapy to the patient while minimizing undesired side-effects produced from the stimulation. Due to physiological diversity, condition differences, and inaccuracies in stimulation lead placement, the parameters may vary between patients, requiring the clinician to individually program stimulation parameters for each patient. This programming process may continue throughout the therapy as patient needs change.

In some examples, a clinician may be assisted in programming through the use of volume of tissue activation (VTA). For example, for a given set of electrical stimulation values and lead positions, the volume of tissue activated by the delivery of electrical stimulation may be calculated and displayed to a clinician via a user interface. Such a volume may represent tissue for which the amplitude of bioelectrical signals of neurons within the tissue may be increased above an activation threshold for a particular patient as a result of the electrical stimulation, thereby activating the neurons via the electrical signals. In some examples, activating neurons of a particular tissue of a patient may treat or manage a patient condition, e.g., by reducing or substantially eliminating one or more undesirable manifestations associated with the condition. By displaying a visual representation of the VTA resulting from a particular set of parameters delivered via one or more electrodes, a clinician may evaluate the location of electrodes and as well as the VTA resulting from a particular set of stimulation parameters to see if the electrical stimulation activates neurons of a desired tissue site. In this sense, VTA may be used to facilitate the programming of therapy and/or implantation of one or more electrodes for delivery of electrical stimulation to a patient.

However, considerations other than that of the volume of activated neurons may additionally or alternatively be used in determining one or more stimulation parameters values and/or electrode location(s) that effectively treat or manage a patient condition via the delivery of electrical stimulation therapy to a patient. In some examples, electrical stimulation delivered to a tissue site may influence the bioelectrical signals of one or more neurons within a tissue, but does not cause the signals to increase above an activation threshold. As described above, neurons within a VSTI may be influenced by the delivery of stimulation via one or more electrodes to a tissue site although the neurons are not activated by the electrical stimulation, e.g., the neurons do not fire action potentials in response to the stimulation. For tissue within VSTI, there may be subtle, but powerful, effects of sub-threshold stimulation that may allow for desynchronization or synchronization of tissue due to the delivery of electrical stimulation via one or more electrodes. In some examples, the volume of neural tissue that is desynchronized or synchronized in a sub-threshold manner can be as large as ten times the directly activated volume. In some examples, neural desynchronization or synchronization may be a mechanism of action of DBS within neural circuits, e.g., by disrupting pathological bioelectrical activity within a neural circuit. For example, desynchronization may occur through effects on phase response relationships between neurons or groups of neurons at a point within a neural circuit. This, in turn, can also alter the neural activities within neural circuits that may be involved in pathological brain activities.

As such, VSTI may be provide a valuable tool to assist in programming electrical stimulation parameters and/or positioning of electrodes for delivery of stimulation to a patient, e.g., to treat or manage a patient disorder, by allowing a clinician to position electrode(s) and/or program one or more parameters of electrical stimulation to provide for the delivery of electrical stimulation that disrupts but does not activate neurons of a target tissue.

In accordance with some examples of this disclosure, a VSTI may be determined for a given set of electrical stimulation parameter values defining electrical stimulation therapy for delivery via one or more electrodes. In some examples, a graphical representation of the determined VSTI may be displayed to a user via a user interface, e.g., as an aspect of guided programming. The display of the VSTI may be presented to a user, such as a clinician, to assist in programming of electrical stimulation by allowing the clinician to visualize the VSTI resulting from delivery of a given electrical stimulation. The VSTI may be shown in conjunction with a representation of the one or more electrodes on an implanted lead. The representation of the VSTI may be displayed in conjunction with an image of an anatomical region representing an area that the electrical stimulation may be delivered to allow the user to visualize the VSTI relative the anatomical region. In some examples, the representation of the VSTI may also be displayed relative to a VTA.

In some examples, the VSTI may be displayed relative to a representation of one or more electrodes used to deliver the stimulation, e.g., along with a representation of the lead carrying the electrodes. The VSTI may change based on the position of the electrodes and leads. In some examples, the displayed image may be used to assist in identifying a desired implant location of electrodes for delivery of stimulation to treat a patient disorder. For example, the display may allow a user to identify a tissue site at which the VSTI for stimulation delivered by the electrodes covers an area that is known to treat a patient disorder by disrupting (e.g., synchronizing or desynchronizing) pathological electrical activity exhibited by neurons of the tissue site. A user may move the location of the electrodes and/or change stimulation parameters, including which electrodes are used to deliver the stimulation, to see different VSTI's for different configurations, e.g., to identify desirable or undesirable configurations.

In some examples, a user may input information indicative of a desired VSTI, e.g., via a user interface presenting an anatomical image and/or electrode location, and one or more processors may determine the electrical stimulation parameter values that will result in the inputted VSTI. In this manner, a user may identify stimulation parameters by defining a desired VSTI rather than sequentially manipulating stimulation parameters values, e.g., in a guess and check fashion, to arrive at the desired VSTI.

As examples of the foregoing, a user may utilize a touch screen to "draw" a desired target VSTI relative to electrode locations and/or one or more target tissue sites. As another example, a user may use drag-and-drop templates that may be selected from a menu of such templates and "dropped" at a desired location within a display screen, such as at a desired position relative to a target tissue site. This type of operation may be accomplished in some examples by an input device such as a stylus. In other cases, a user's finger or some other type of pointer may be used. VSTI templates may be available from a menu of templates of varying sizes and shapes to allow a user to readily choose a representation of desired VSTI. In some cases, once a representation of a VSTI has been provided within a display relative to target tissue and/or an electrode representation, the size and/or shape of that VSTI representation may be changed by allowing a user to drag a boundary of the VSTI area using a point-and-click device, a drawing instrument contacting a touch screen, or a user's finger. In yet other cases, gesture based control may be used to expand and/or contract at least a portion of a VSTI area on a display screen, as by moving the thumb and index fingers apart from one another to expand the area, or by pinching those fingers together to contract the area.

According to the foregoing examples in which a user provides input indicating a position, size, and/or shape of a VSTI, the system may automatically determine parameters for electrical stimulation. Such parameters include values for amplitude (voltage/current), duration (e.g., pulse width), and frequency (e.g., pulse rate), electrode polarity, electrode vector used to deliver the stimulation (e.g., for unipolar, bipolar, or multipolar stimulation). Other parameters may include a waveform shape if a continuous waveform will be delivered rather than pulse-based stimulation, burst characteristics, and so on to achieve the desired VSTI. This automatic determination of parameters may be accomplished by a best-fit method that iteratively "tries" multiple parameter sets to determine which one yields a VSTI that best approximates the desired target VSTI. The VSTI that is associated with a given parameter set may be determined using various techniques described in detail below, including, but not limited to, modeling techniques and sensing techniques.

Alternatively, derivation of parameters that will result in the desired VSTI may be accomplished using equations or lookup tables that directly map a change in VSTI area to a corresponding change in one or more stimulation parameters. Such equations and/or lookup tables may be developed using the iterative approach discussed above (e.g., using modeling to derive VSTI from parameter sets) for instance. In one case, the equations and/or lookup tables that are used to derive stimulation parameters based on a desired target VSTI may even be developed to take into account patient-specific characteristics of the tissue at the target site as determined based on tissue scans or other diagnostic tools (e.g., MRI, CT, etc.).

Once a given set of electrical stimulation parameters values have been identified either automatically or by user input, the user may program a medical device to deliver electrical stimulation to a patient according to the determined values. Additionally, once a desired implant location has been determined per the process described above, a clinician may actually implant a lead based on the determination. In some examples, VSTI may be displayed during the implant procedure to assist a clinician in identifying a desired implant location during the procedure, e.g., instead of beforehand.

In an example wherein VSTI is determined from a provided parameter set, a VSTI may be determined using one or more suitable modeling techniques. VSTI may be modeled based on electrical stimulation parameters as the VSTI may be a function of the values of the parameters defining electrical stimulation. Electrical stimulation parameters used when determining the VSTI include values for amplitude (voltage/current), duration (e.g., pulse width), and frequency (e.g., pulse rate), electrode polarity, electrode vector used to deliver the stimulation (e.g., for unipolar, bipolar, or multipolar stimulation). Tissue characteristics (such as tissue impedance) may also be taken into consideration for modeling of the VSTI. In some examples, neuron geometry and orientation in 3D space can also be incorporated in more detailed examples.

As noted above, a determined VSTI may be displayed relative to an image representing an anatomical region of a tissue for implant of one or more stimulation electrodes. In some examples, an atlas image or other non-patient specific image of the region may be used. In other examples, an actual image of the anatomical region of the patient may be used (e.g., a CT or MRI image). In other examples, a morphed atlas image may be used. A morphed atlas image combines both non-patient specific and actual images of the patient to form a single image of an anatomical region.

In some examples, VSTI may be determined for a given stimulation by actually sensing the electrical activity of tissue at one or more locations in conjunction with the delivery of electrical stimulation. For example, based on the sensed activity, it may be determined whether or not the delivered electrical stimulation disrupted (desynchronized or synchronized) electrical activity of neurons at the sensing site. Additionally, it may be determined whether or not neurons at the sensing site where activated by the stimulation or not disrupted by the stimulation. In this manner, the actual VSTI resulting from the stimulation may be identified, e.g., along with the volume of tissue activated (VTA). The determined VSTI and/or VTA may be displayed to a user via a user interface, as describe herein.

FIG. 1 is a conceptual diagram illustrating an example therapy system 10 in accordance with examples of the disclosure. In FIG. 1, example therapy system 10 may deliver electrical stimulation therapy to treat or otherwise manage a patient condition, such as, e.g., a movement disorder of patient 12. For example, therapy system 10 may deliver electrical stimulation to treat or otherwise manage Parkinson's disease, e.g., by reducing or preventing the manifestation of symptoms exhibited by patients suffering from Parkinson's disease. However, system 10 may be used to manage or otherwise treat symptoms of other patient disorders, such as, but not limited to, essential tremor or other movement disorders, psychological disorders, mood disorders, seizure disorders, chronic pain, or other neurogenerative impairment. In one example, such techniques may be employed to provide therapy to patient to manage Alzheimer's disease. Patient 12 ordinarily will be a human patient. In some cases, however, therapy system 10 may be applied to other mammalian or non-mammalian non-human patients.

Therapy system 10 includes medical device programmer 14, implantable medical device (IMD) 16, lead extension 18, and lead 20 with set of electrodes 26. IMD 16 includes a stimulation therapy module that includes a stimulation generator that generates and delivers electrical stimulation therapy to one or more regions of brain 28 of patient 12 via one or more of electrodes 26 of lead 20. In the example shown in FIG. 1, therapy system 10 may be referred to as a deep brain stimulation (DBS) system because IMD 16 provides electrical stimulation therapy directly to tissue within brain 28, e.g., a tissue site under the dura mater of brain 28. In other examples, lead 20 may be positioned to deliver therapy to a surface of brain 28 (e.g., the cortical surface of brain 28).

In some examples, delivery of stimulation to one or more regions of brain 28, such as an anterior nucleus (AN), thalamus or cortex of brain 28, provides an effective treatment to manage a disorder of patient 12. In some examples, IMD 16 may provide cortical stimulation therapy to patient 12, e.g., by delivering electrical stimulation to one or more tissue sites in the cortex of brain 28. In cases in which IMD 16 delivers electrical stimulation to brain 28 to treat a movement disorder such as Parkinson's disease by disrupting brain signals occurring at pathological frequencies, target stimulation sites may include one or more basal ganglia sites, including, e.g., subthalamic nucleus (STN), globus pallidus interna (GPi), globus pallidus externa (GPe), pedunculopontine nucleus (PPN), thalamus, substantia nigra pars reticulata (SNr), internal capsule, and/or motor cortex.

In the example shown in FIG. 1, IMD 16 may be implanted within a subcutaneous pocket above the clavicle of patient 12. In other examples, IMD 16 may be implanted within other regions of patient 12, such as a subcutaneous pocket in the abdomen or buttocks of patient 12, or proximate the cranium of patient 12. Implanted lead extension 18 is coupled to IMD 16 via connector block 30 (also referred to as a header), which may include, for example, electrical contacts that electrically couple to respective electrical contacts on lead extension 18. The electrical contacts electrically couple the electrodes 26 carried by lead 20 to IMD 16. Lead extension 18 in combination with lead 20 traverses from the implant site of IMD 16 within a chest cavity of patient 12, along the neck of patient 12 and through the cranium of patient 12 to access brain 28. Generally, IMD 16 is constructed of a biocompatible material that resists corrosion and degradation from bodily fluids. IMD 16 may comprise a hermetic housing 34 to substantially enclose components, such as a processor, therapy module, and memory.

Lead 20 may be implanted within the right and/or left hemispheres of brain 28 in order to deliver electrical stimulation to one or more regions of brain 28, which may be selected based on many factors, such as the type of patient condition for which therapy system 10 is implemented to manage. Other implant sites for lead 20 and IMD 16 are contemplated. For example, IMD 16 may be implanted on or within cranium 32 or lead 20 may be implanted within only one hemisphere. Although system 10 is shown including only a single lead, in some examples, system 10 may include multiple leads, e.g., two leads, to deliver stimulation to one or both hemispheres of brain 28.

Lead 20 may be positioned to deliver electrical stimulation to one or more target tissue sites within brain 28 to manage patient symptoms associated with a disorder of patient 12. Lead 20 may be implanted to position electrodes 26 at one or more desired locations of brain 28 through a hole in cranium 32. Lead 20 may be placed at any location within brain 28 such that electrodes 26 are capable of providing electrical stimulation to target tissue sites within brain 28 during treatment. For example, in the case of Parkinson's disease, for example, lead 20 may be implanted to deliver electrical stimulation to one or more basal ganglia sites, including, e.g., subthalamic nucleus (STN), globus pallidus interna (GPi), globus pallidus externa (GPe), pedunculopontine nucleus (PPN), thalamus, substantia nigra pars reticulata (SNr), internal capsule, and/or motor cortex.

As noted above, although FIG. 1 illustrates system 10 as including one lead 20 coupled to IMD 16 via lead extension 18, in some examples, system 10 may include two leads or more than two leads. Lead 20 may deliver electrical stimulation to treat any number of neurological disorders or diseases in addition to movement disorders, such as seizure disorders or psychiatric disorders. Examples of movement disorders include a reduction in muscle control, motion impairment or other movement problems, such as rigidity, bradykinesia, rhythmic hyperkinesia, nonrhythmic hyperkinesia, dystonia, tremor, and akinesia. Movement disorders may be associated with patient disease states, such as Parkinson's disease or Huntington's disease. Examples of psychiatric disorders include MDD, bipolar disorder, anxiety disorders, post traumatic stress disorder, dysthymic disorder, and OCD.

Lead 20 may be implanted within a desired location of brain 28 via any suitable technique. Lead 20 may be placed at any location within brain 28 such that electrodes 26 of lead 20 are capable of providing electrical stimulation to targeted tissue during treatment. As will be described further below, the implant location of lead 20 may be identified using one or more techniques utilizing the determination and display of VSTI resulting in the delivery of a given electrical stimulation via one or more of electrodes 26.

Electrical stimulation generated from the stimulation generator (not shown) within the therapy module of IMD 16 may help prevent the onset of events associated with the patient's disorder or mitigate symptoms of the disorder.

In the examples shown in FIG. 1, electrodes 26 of lead 20 are shown as ring electrodes. Ring electrodes may be relatively easy to program and are typically capable of delivering an electrical field to any tissue adjacent to lead 20. In other examples, electrodes 26 of lead 20 may have different configurations. For example, electrodes 26 of lead 20 may have a complex electrode array geometry that is capable of producing shaped electrical fields. The complex electrode array geometry may include multiple electrodes (e.g., partial ring or segmented electrodes) around the perimeter of lead 20, rather than a ring electrode. In this manner, electrical stimulation may be directed to a specific direction from lead 20 to enhance therapy efficacy and reduce possible adverse side effects from stimulating a large volume of tissue.

In some examples, outer housing 34 of IMD 16 may include one or more stimulation and/or sensing electrodes. For example, housing 34 can comprise an electrically conductive material that is exposed to tissue of patient 12 when IMD 16 is implanted in patient 12, or an electrode can be attached to housing 34. In alternative examples, lead 20 may have shapes other than an elongated cylinder as shown in FIG. 1. For example, lead 20 may be a paddle lead, spherical lead, bendable lead, or any other type of shape effective in treating patient 12.

IMD 16 may deliver electrical stimulation therapy to brain 28 of patient 12 according to one or more stimulation therapy programs. A therapy program may define one or more electrical stimulation parameter values for therapy generated and delivered from IMD 16 to brain 28 of patient 12. Where IMD 16 delivers electrical stimulation in the form of electrical pulses, for example, the stimulation therapy may be characterized by selected pulse parameters, such as pulse amplitude, pulse rate, and pulse width. In addition, if different electrodes are available for delivery of stimulation, the therapy may be further be characterized by different electrode combinations, which can include selected electrodes and their respective polarities. The VSTI resulting from electrical stimulation delivered via one or more of electrodes 26 may be a function of such stimulation parameters.

The exact therapy parameter values of the stimulation therapy that helps to manage or treat a patient disorder may be specific for the particular target stimulation site (e.g., the region of the brain) involved as well as the particular patient and patient condition. As will be described below, one or more of electrodes 26 may be positioned such that the delivery of a given electrical stimulation results in a VSTI that includes one more desired anatomical regions. For example, as a result of the stimulation, neurons exhibiting pathological bioelectrical signals within the VSTI may be desynchronized or otherwise disrupted in a manner that eliminates the pathological activity.

In addition to delivering therapy to manage a disorder of patient 12, therapy system 10 may monitor one or more bioelectrical brain signals of patient 12. For example, IMD 16 may include a sensing module that senses bioelectrical brain signals within one or more regions of brain 28. In the example shown in FIG. 1, the signals generated by electrodes 26 may be conducted to the sensing module within IMD 16 via conductors within the lead 20. In some examples, a processor of IMD 16 may sense the bioelectrical signals within brain 28 of patient 12, and control delivery of electrical stimulation therapy to brain 28 via electrodes 26 when the bioelectrical brain signals are oscillating at a pathological frequency. For neurons having a VSTI resulting from the electrical stimulation, the electrical stimulation may be configured to disrupt the pathological activity, e.g., via desynchronization or synchronization, rather the actually activating the neurons.

In some examples, the sensing module of IMD 16 may receive the bioelectrical signals from electrodes 26 or other electrodes positioned to monitored brain signals of patient 12. Electrodes 26 may also be used to deliver electrical stimulation from the therapy module to target sites within brain 28 as well as sense brain signals within brain 28. However, IMD 16 can also use separate sensing electrodes to sense the bioelectrical brain signals. In some examples, the sensing module of IMD 16 may sense bioelectrical brain signals via one or more of the electrodes 26 that are also used to deliver electrical stimulation to brain 28. In other examples, one or more of electrodes 26 may be used to sense bioelectrical brain signals while one or more different electrodes 26 may be used to deliver electrical stimulation.

Depending on the particular stimulation electrodes and sense electrodes used by IMD 16, IMD 16 may monitor brain signals and deliver electrical stimulation at the same region of brain 28 or at different regions of brain 28. In some examples, the electrodes used to sense bioelectrical brain signals may be located on the same lead used to deliver electrical stimulation, while in other examples, the electrodes used to sense bioelectrical brain signals may be located on a different lead than the electrodes used to deliver electrical stimulation. In some examples, a brain signal of patient 12 may be monitored with external electrodes, e.g., scalp electrodes or electrodes implanted just under the scalp. Moreover, in some examples, the sensing module that senses bioelectrical brain signals of brain 28 (e.g., the sensing module that generates an electrical signal indicative of the activity within brain 28) is in a physically separate housing from outer housing 34 of IMD 16. However, in the example shown in FIG. 1 and the example primarily referred to herein for ease of description, the sensing module and therapy module of IMD 16 are enclosed within a common outer housing 34.

The bioelectrical brain signals monitored by IMD 16 may reflect changes in electrical current produced by the sum of electrical potential differences across brain tissue. Examples of the monitored bioelectrical brain signals include, but are not limited to, an electroencephalogram (EEG) signal, an electrocorticogram (ECoG) signal, a local field potential (LFP) sensed from within one or more regions of a patient's brain and/or action potentials from single cells within the patient's brain.

External programmer 14 wirelessly communicates with IMD 16 as needed to provide or retrieve therapy information. Programmer 14 is an external computing device that the user, e.g., the clinician and/or patient 12, may use to communicate with IMD 16. For example, programmer 14 may function as a clinician programmer that the clinician uses to communicate with IMD 16 and program one or more therapy programs for IMD 16. Additionally or alternatively, programmer 14 may function as a patient programmer that allows patient 12 to select programs and/or view and modify therapy parameters. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device or another input mechanism that allows the user to navigate though the user interface of programmer 14 and provide input. If programmer 14 includes buttons and a keypad, the buttons may be dedicated to performing a certain function, i.e., a power button, or the buttons and the keypad may be soft keys that change in function depending upon the section of the user interface currently viewed by the user.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as a secure medical device programmer 14. A wireless adapter coupled to the computing device may enable secure communication between the computing device and IMD 16.

When programmer 14 is configured for use by the clinician, programmer 14 may be used to transmit initial programming information to IMD 16. This initial information may include hardware information, such as the type of lead 20, the arrangement of electrodes 26 on lead 20, the position of lead 20 within brain 28, initial programs defining therapy parameter values, and any other information that may be useful for programming into IMD 16. Programmer 14 may also be capable of completing functional tests (e.g., measuring the impedance of electrodes 26 of lead 20).

The clinician may also store therapy programs within IMD 16 with the aid of programmer 14. During a programming session, the clinician may determine one or more therapy programs that may provide efficacious therapy to patient 12 to address symptoms associated with the movement disorder (or other patient condition). For example, the clinician may select one or more electrode combinations with which stimulation is to be delivered to brain 28. During the programming session, patient 12 may provide feedback to the clinician as to the efficacy of the specific program being evaluated or the clinician may evaluate the efficacy based on one or more physiological parameters of patient (e.g., heart rate, respiratory rate or muscle activity). Programmer 14 may assist the clinician in the creation/identification of therapy programs by providing a methodical system for identifying potentially beneficial therapy parameter values.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12. In this manner, programmer 14 may only allow patient 12 to adjust values for certain therapy parameters or set an available range of values for a particular therapy parameter.

Programmer 14 may also provide an indication to patient 12 when therapy is being delivered, when patient input has triggered a change in therapy or when the power source within programmer 14 or IMD 16 needs to be replaced or recharged. For example, programmer 14 may include an alert LED, may flash a message to patient 12 via a programmer display, generate an audible sound or somatosensory cue to confirm patient input was received, e.g., to indicate a patient state or to request that the patient manually modify a therapy parameter.

Whether programmer 14 is configured for clinician or patient use, programmer 14 is configured to communicate to IMD 16 and, optionally, another computing device, via wireless communication. Programmer 14, for example, may communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

One or more processors of programmer 14 may be used to determine and/or display a VSTI for electrical stimulation that may be delivered to patient 12 via IMD 16 and lead 20. As will be described below, a graphical representation of a VSTI may be displayed via a user interface of programmer 14 to a user, e.g., to assist a clinician in identifying desired therapy parameter values and/or stimulation electrode locations for delivery of electrical stimulation therapy. One or more processors, such as a processor of IMD 16, processor of programmer 14, and/or a processor of another device may be used to determine the VSTI displayed via the user interface. In one example, processors of multiple devices may participate in various steps to determine the VSTI that is displayed. For instance, a processor or other control circuit of an IMD may perform some of the steps involved in determining the VST, while other steps are performed by a processor or other control circuit of an external device (e.g., a programmer). In this manner, more than one device may be involved in performing functions as described herein.

Therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. In some cases, the trial stimulation system may include an external device that is coupled wirelessly to one or more leads that are fully-implanted. If the trial stimulator indicates DBS system 10 provides effective treatment to patient 12, the clinician may implant a chronic stimulator within patient 12 for relatively long-term treatment.

Figure 2:
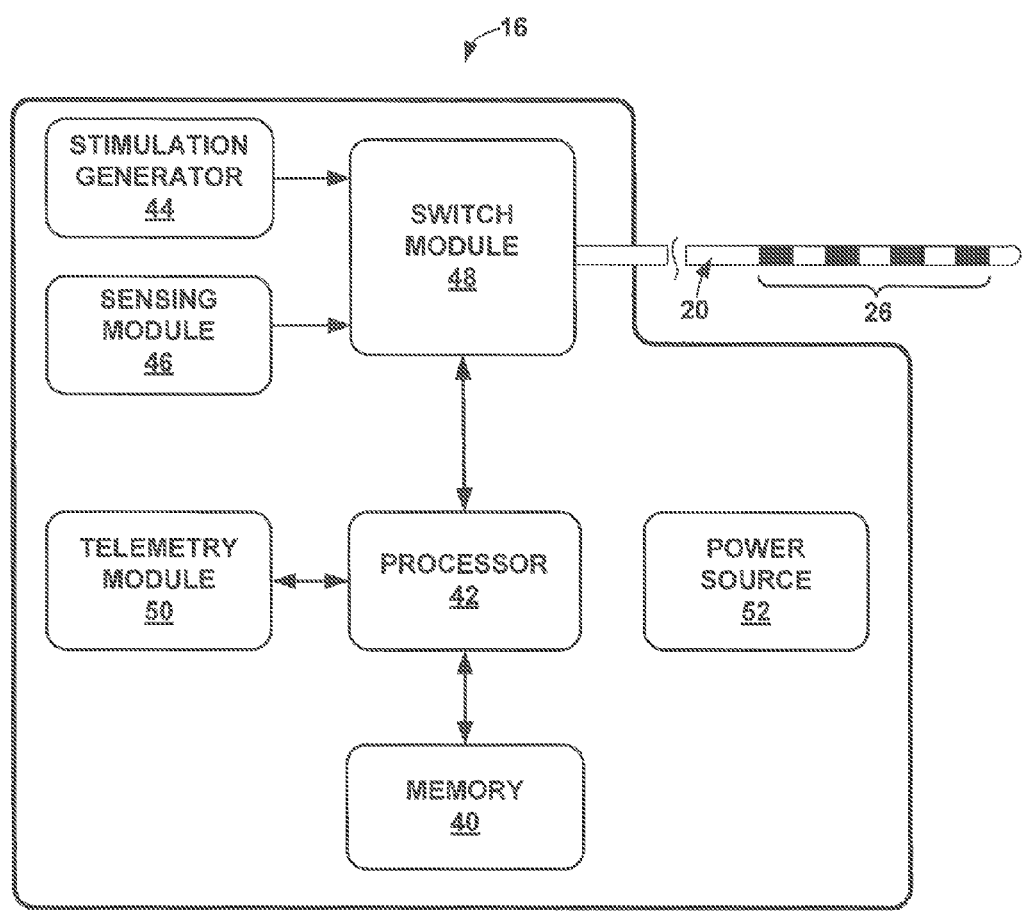
FIG. 2 is functional block diagram illustrating components of an example medical device.

FIG. 2 is a functional block diagram illustrating components of an example IMD 16. In the example shown in FIG. 2, IMD 16 includes memory 40, processor 42, stimulation generator 44, sensing module 46, switch module 48, telemetry module 50, and power source 52. Processor 42 may include any one or more microprocessors, controllers, digital signal processors (DSPs), application specific integrated circuits (ASICs), field-programmable gate arrays (FPGAs), and discrete logic circuitry. The functions attributed to processors described herein, including processor 42, may be provided by a hardware device and embodied as software, firmware, hardware, or any combination thereof.

In the example shown in FIG. 2, sensing module 46 senses bioelectrical brain signals of patient 12 via select combinations of electrodes 26. Sensing module 46 may include circuitry that measures the electrical activity of a particular region, e.g., an anterior nucleus, thalamus or cortex of brain 24 via select electrodes 26. For treatment of Parkinson's disease, sensing module 46 may be configured to measure the electrical activity of the subthalamic nucleus (STN), globus pallidus interna (GPi), globus pallidus externa (GPe), and/or other areas of the basal ganglia.

Sensing module 46 may sample the bioelectrical brain signal substantially continuously or at regular intervals, such as, but not limited to, a frequency of about 1 Hz to about 1000 Hz, such as about 250 Hz to about 1000 Hz or about 500 Hz to about 1000 Hz. Sensing module 46 includes circuitry for determining a voltage difference between two electrodes 26, which generally indicates the electrical activity within the particular region of brain 24. One of the electrodes 26 may act as a reference electrode, and, if sensing module 46 is implanted within patient 12, a housing of IMD 16, or the sensing module in examples in which sensing module 46 is separate from IMD 16, may include one or more electrodes that may be used to sense bioelectrical brain signals.

The output of sensing module 46 may be received by processor 42. In some cases, processor 42 may apply additional processing to the bioelectrical signals, e.g., convert the output to digital values for processing and/or amplify the bioelectrical brain signal. In addition, in some examples, sensing module 46 or processor 42 may filter the signal from the selected electrodes 26 in order to remove undesirable artifacts from the signal, such as noise from cardiac signals generated within the body of patient 12. Although sensing module 46 is incorporated into a common outer housing with stimulation generator 44 and processor 42 in FIG. 2, in other examples, sensing module 46 is in a separate outer housing from the outer housing of IMD 16 and communicates with processor 42 via wired or wireless communication techniques. In some examples, a bioelectrical brain signal may be sensed via external electrodes (e.g., scalp electrodes).

In some examples, sensing module 46 may monitor one or more physiological parameters of a patient other than that of bioelectrical brain signals, which are indicative of a patient disorder, e.g., in combination with the monitored bioelectrical brains signals of the patients. Suitable patient physiological parameters may include, but are not limited to, muscle tone (e.g., as sensed via electromyography (EMG)), eye movement (e.g., as sensed via electroculography (EOG) or EEG), and body temperature. In some examples, patient movement may be monitored via actigraphy. In one example, processor 42 may monitor an EMG signal reflective of the muscle tone of patient 12 to identify physical movement of the patient. Alternatively or additionally, processor 42 may monitor the physical movement of a patient via one or more motion sensors, such as, e.g., one or more single or multi-axis accelerometer devices.

Memory 40 may include any volatile or non-volatile media, such as a random access memory (RAM), read only memory (ROM), non-volatile RAM (NVRAM), electrically erasable programmable ROM (EEPROM), flash memory, and the like. Memory 40 may store computer-readable instructions that, when executed by processor 42, cause IMD 16 to perform various functions described herein. Memory 40 may be considered, in some examples, a non-transitory computer-readable storage medium comprising instructions that cause one or more processors, such as, e.g., processor 42, to implement one or more of the example techniques described in this disclosure. The term "non-transitory" may indicate that the storage medium is not embodied in a carrier wave or a propagated signal. However, the term "non-transitory" should not be interpreted to mean that memory 40 is non-movable. As one example, memory 40 may be removed from IMD 16, and moved to another device. In certain examples, a non-transitory storage medium may store data that can, over time, change (e.g., in RAM).

In the example shown in FIG. 2, the set of electrodes 26 of lead 20 includes four electrodes. Processor 42 controls switch module 48 to sense bioelectrical brain signals with selected combinations of electrodes 26. In particular, switch module 48 may create or cut off electrical connections between sensing module 46 and selected electrodes 26 in order to selectively sense bioelectrical brain signals, e.g., in particular portions of brain 28 of patient 12.

Processor 42 may also control switch module 48 to apply stimulation signals generated by stimulation generator 44 to selected combinations of electrodes 26. In particular, switch module 48 may couple stimulation signals to selected conductors within lead 20, which, in turn, deliver the stimulation signals across selected electrodes 26. Switch module 48 may be a switch array, switch matrix, multiplexer, or any other type of switching module configured to selectively couple stimulation energy to selected electrodes 26 and to selectively sense bioelectrical brain signals with selected electrodes 26. Hence, stimulation generator 44 may be coupled to electrodes 24, 26 via switch module 48 and conductors within lead 20. In some examples, however, IMD 16 does not include switch module 48. In some examples, IMD 16 may include separate stimulation generators, e.g., current sources and sinks, for each individual electrode (e.g., instead of a single stimulation generator) such that switch module 48 may not be necessary.

Stimulation generator 44 may be a single channel or multi-channel stimulation generator. For example, stimulation generator 44 may be capable of delivering, a single stimulation pulse, multiple stimulation pulses or a continuous signal at a given time via a single electrode combination or multiple stimulation pulses at a given time via multiple electrode combinations. In some examples, however, stimulation generator 44 and switch module 48 may be configured to deliver multiple channels on a time-interleaved basis. For example, switch module 48 may serve to time divide the output of stimulation generator 44 across different electrode combinations at different times to deliver multiple programs or channels of stimulation energy to patient 12.

Telemetry module 50 may support wireless communication between IMD 16 and an external programmer 14 or another computing device under the control of processor 42. Processor 42 of IMD 16 may, for example, transmit bioelectrical brain signals, seizure probability metrics for particular sleep stages, a seizure probability profile for patient 12, and the like via telemetry module 50 to a telemetry module within programmer 14 or another external device. Telemetry module 50 in IMD 16, as well as telemetry modules in other devices and systems described herein, such as programmer 14, may accomplish communication by radiofrequency (RF) communication techniques, which may be short-range, long-range, or mid-range (e.g., arm's length) techniques. For instance, telemetry module 50 may communicate with external programmer 14 via proximal inductive interaction of IMD 16 with programmer 14. Accordingly, telemetry module 50 may send information to external programmer 14 on a continuous basis, at periodic intervals, or upon request from IMD 16 or programmer 14.

Power source 52 delivers operating power to various components of IMD 16. Power source 52 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 3:
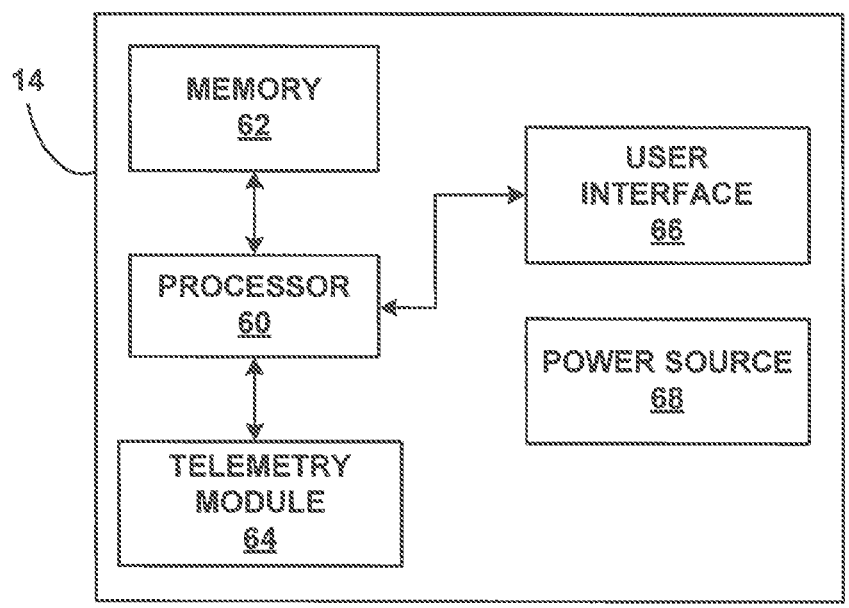
FIG. 3 is a functional block diagram illustrating components of an example medical device programmer.

FIG. 3 is a conceptual block diagram of an example external medical device programmer 14, which includes processor 60, memory 62, telemetry module 64, user interface 66, and power source 68. Processor 60 controls user interface 66 and telemetry module 64, and stores and retrieves information and instructions to and from memory 62. Programmer 14 may be configured for use as a clinician programmer and/or a patient programmer. Processor 60 may comprise any combination of one or more processors including one or more microprocessors, DSPs, ASICs, FPGAs, or other equivalent integrated or discrete logic circuitry. Accordingly, processor 60 may include any suitable structure, whether in hardware, software, firmware, or any combination thereof, to perform the functions ascribed herein to processor 60.

A user, such as a clinician or patient 12, may interact with programmer 14 through user interface 66. User interface 66 includes a display (not shown), such as a LCD or LED display or other type of screen, to present information related to treatment of disorder of patient 12. User interface 66 may also include an input mechanism to receive input from the user. The input mechanisms may include, for example, buttons, a keypad (e.g., an alphanumeric keypad), a peripheral pointing device or another input mechanism that allows the user to navigate though user interfaces presented by processor 60 of programmer 14 and provide input.

Memory 62 may include instructions for operating user interface 66 and telemetry module 64, and for managing power source 68. Memory 62 may also store any therapy data retrieved from IMD 16 during the course of therapy, as well as sensed bioelectrical brain signals. The clinician may use this therapy data to determine the progression of the patient condition in order to plan future treatment. Memory 62 may include any non-transitory volatile or nonvolatile memory, such as RAM, ROM, EEPROM or flash memory. Memory 62 may also include a removable memory portion that may be used to provide memory updates or increases in memory capacities. A removable memory may also allow sensitive patient data to be removed before programmer 14 is used by a different patient.

Memory 62 may be considered, in some examples, a non-transitory computer-readable storage medium comprising instructions that cause one or more processors, such as, e.g., processor 60, to implement one or more of the example techniques described in this disclosure. The term "non-transitory" may indicate that the storage medium is not embodied in a carrier wave or a propagated signal. However, the term "non-transitory" should not be interpreted to mean that memory 62 is non-movable or that it necessarily maintains information with the removable of power to the storage device. As one example, memory 62 may be removed from programmer 14, and moved to another device. In certain examples, a non-transitory storage medium may store data that can, over time, change (e.g., in RAM).

Wireless telemetry in programmer 14 may be accomplished by RF communication or proximal inductive interaction of external programmer 14 with IMD 16. This wireless communication is possible through the use of telemetry module 64. Accordingly, telemetry module 64 may be similar to the telemetry module contained within IMD 16. In alternative examples, programmer 14 may be capable of infrared communication or direct communication through a wired connection. In this manner, other external devices may be capable of communicating with programmer 14 without needing to establish a secure wireless connection.

Power source 68 may deliver operating power to the components of programmer 14. Power source 68 may include a battery and a power generation circuit to produce the operating power. In some examples, the battery may be rechargeable to allow extended operation.

As describe herein, processor 60 of programmer 14 may be used to determine and/or display a VSTI for electrical stimulation that may be delivered to patient 12 via IMD 16 and lead 20. In some examples, a graphical representation of a VSTI may be displayed via a user interface of programmer 14 to a user, e.g., to assist a clinician in identifying desired therapy parameter values and/or location of electrodes 26. One or more processors, such as a processor of IMD 16, processor of programmer 14, and/or a processor of another device may be used to determine the VSTI displayed via the user interface. Programmer 14 may be used by a user, such as a clinician, to identify desirable electrical stimulation parameters and/or electrode location in view of the VSTI displayed on user interface 66, e.g., according to one or more of the examples described herein. In some examples, a user may be allowed to provide information defining the VSTI, and the system may automatically determine one or more parameters for stimulation based on the VSTI.

FIGS. 4-13 illustrate various aspects of the disclosure. For ease of illustration, some of the examples of FIGS. 4-13 are primarily described with regard to therapy system 10. However, the examples are not limited as such and may be implemented using any suitable therapy system. Moreover, while the following examples are described primarily as being performed via processor 60 of programmer 14, such examples may be carried out entirely or in combination with any other processor, e.g., such as processor 42 of IMD 16.

Figure 4:
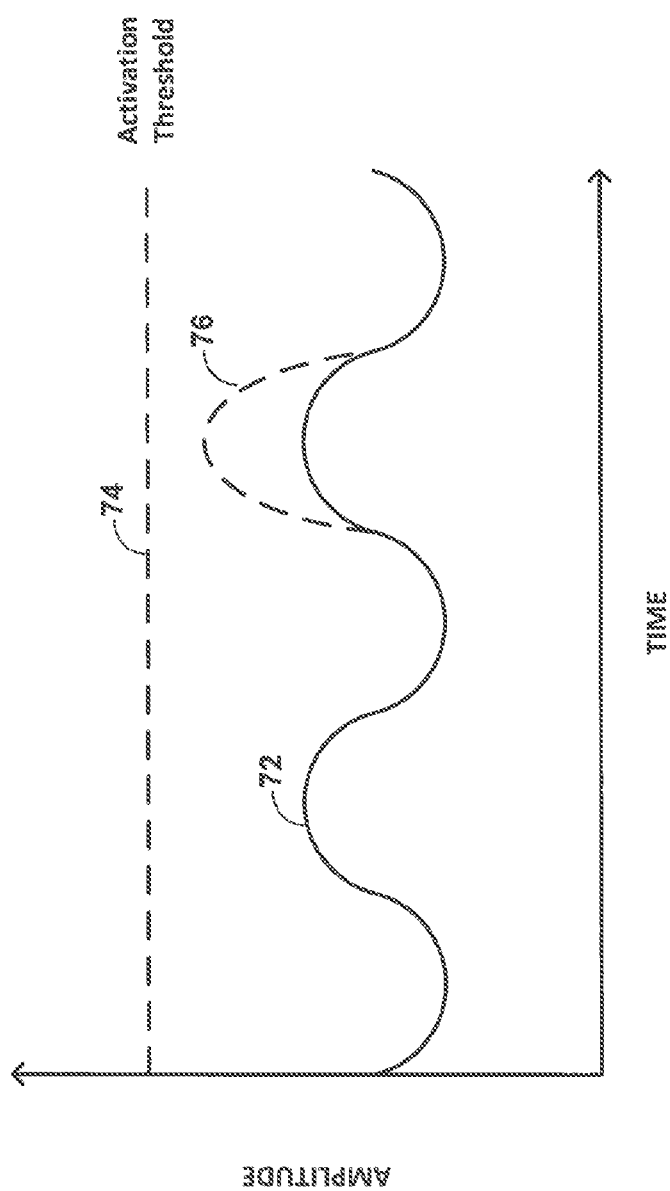
FIG. 4 is conceptual diagram illustrating the influence of example sub-activation threshold stimulation.

FIG. 4 is conceptual plot illustrating the influence of example sub-activation threshold electrical stimulation in terms of amplitude per unit time. Solid line 72 represents the bioelectrical brain signal exhibited by neurons at a given tissue site in brain 28 of patient 12. Dashed-line 76 represents the disruption of bioelectrical brain signal 72 due to the delivery of electrical stimulation to brain 28 from IMD 16 via one or more electrodes 26. Although the amplitude of the electrical signal is increased due the delivery of electrical stimulation, the disruption does not cause the electrical signal to exceed activation threshold 74 for a particular patient or for a group of patients. An activation threshold may be, for example, a threshold intensity level (e.g., a function of one or more stimulation parameter values, such as an amplitude, frequency, or both) at which neurons are activated by the electrical stimulation. In this sense, the neurons within the tissue site exhibiting the electrical behavior represented by the plot of FIG. 4 may be characterized as not being within the VTA for the electrical stimulation. However, as indicated in FIG. 4, the electrical stimulation still disrupts the electrical activity (e.g., in a manner that allows for desynchronization and/or synchronization of pathological electrical activity exhibited at the tissue site) of the neurons at the tissue site. In this sense, the tissue site may be characterized as being within the VSTI of the stimulation.

Figure 5:
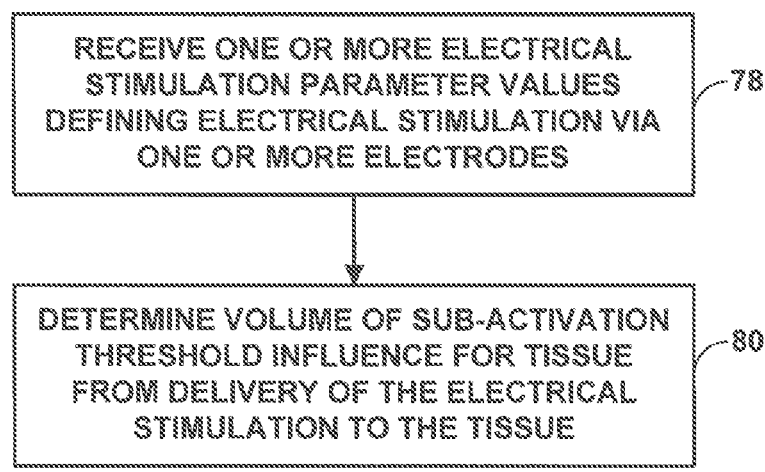
FIG. 5 is a flow diagram illustrating an example technique for determining a VSTI.

FIG. 5 is a flowchart illustrating an example technique for determining a VSTI for electrical stimulation. As shown, processor 60 may receive one or more electrical stimulation parameter values, e.g., from a user via user interface 66, to define an electrical stimulation therapy that may be delivered to patient 12 via one or more of electrodes 26 (78). The electrical stimulation may be defined by values for one or more of amplitude (voltage/current), duration (e.g., pulse width), and frequency (e.g., pulse rate), electrode polarity, electrode vector used to deliver the stimulation (e.g., for unipolar, bipolar, or multipolar stimulation). In some examples, processor 60 may retrieve one therapy program stored on memory 40 of IMD 16 and/or memory 62 of programmer 14 to define the electrical stimulation. Additionally or alternatively, using user interface 66, a user such as a clinician may input values for one or more electrical stimulation parameters to define new stimulation or modify the values for one or more electrical stimulation parameters, e.g., of an existing therapy program.

Based on the received value(s), processor 60 may determine the VSTI for the electrical stimulation defined by the one or more electrical stimulation parameter values. The VSTI may be determined using any suitable modeling technique. Electrical stimulation parameters used when determining the VSTI include values for amplitude (voltage/current), duration (e.g., pulse width), and frequency (e.g., pulse rate), electrode polarity, electrode vector used to deliver the stimulation (e.g., unipolar, bipolar, or multipolar stimulation vectors). Additionally, stimulation electrode location and/or tissue characteristics (such as tissue impedance) or other factor that may be a function of brain location may also be taken into consideration for modeling of the VSTI. In some examples, to determine VSTI, modulating factors, such as, e.g., pharmacological agents being taken by a patient, patient age, patient gender, and other physiological changes to tissue (degeneration, density and/or structural changes to tissue fibers) associated with disease states such as, e.g., Alzheimer's disease or other degenerative disorders, may be taken into consideration.

Suitable modeling techniques may range from simple to complex. In some examples, modeling the responses of neurons may be a two-step process that includes a first step of determining of the electric field generated by the stimulation, and a second step of estimating the neuronal response to the applied electric field. In a relatively simple case, a spherical cell or nerve axon may be modeled as individual elements, and the electrical field may be estimated using a point source model or using a more detailed finite element model. The distribution of the neuronal elements (e.g., axons) may be uniform or non-uniform around the electrode. In more complex models, more realistic neuron geometry and orientation information may be incorporated into the model. In a still more complex example, neuronal connectivity (e.g. synapses, gap junctions) may be additionally modeled in order to generate a network model of the relevant brain circuit(s). The polarization of the neuronal elements may be monitored at a specific point (e.g. axon node, cell body) and the VSTI may be estimated by indicating a threshold value of polarization that the transmembrane potential must reach in order to be included in the VSTI. For example, a threshold value of 10 mV change in the transmembrane potential may be used to define the VSTI, in which case all neurons or neuronal elements that exceed this threshold value will be included in the VSTI. The selection of such a threshold value may cause relative changes in the size of the VSTI.

In other examples, the VSTI resulting from electrical stimulation may be modeled based on sensing of electrical activity in conjunction with actual delivery of electrical stimulation to a patient. For example, in such a case, processor 40 may sense the bioelectrical activity exhibited at one or more tissue locations via sensing module 46 and one or more of electrodes 26. During substantially the same period of time processor 40 is sensing the bioelectrical activity, processor 40 may control stimulation generator to deliver electrical stimulation to one or more tissue sites via one or more of electrodes 26. Based on the sensed electrical activity, processor 40 may determine the VSTI for the electrical stimulation (or at least a rough estimate, depending on the number of sensing locations) based on the influence the electrical stimulation had, if any, at the one or more sensing locations. For example, processor 40 may determine the VSTI for the delivered electrical stimulation in view of a measured functional synaptic volume. Synaptic volume may be measured using any suitable technique including one or more of the examples described in U.S. patent application Ser. No. 13/446,459, to Nelson et al., entitled "METHOD AND APPARATUS FOR ASSESSING NEURAL ACTIVATION," filed Apr. 13, 2012, the entire content of which is incorporated herein by reference.

Figure 6:
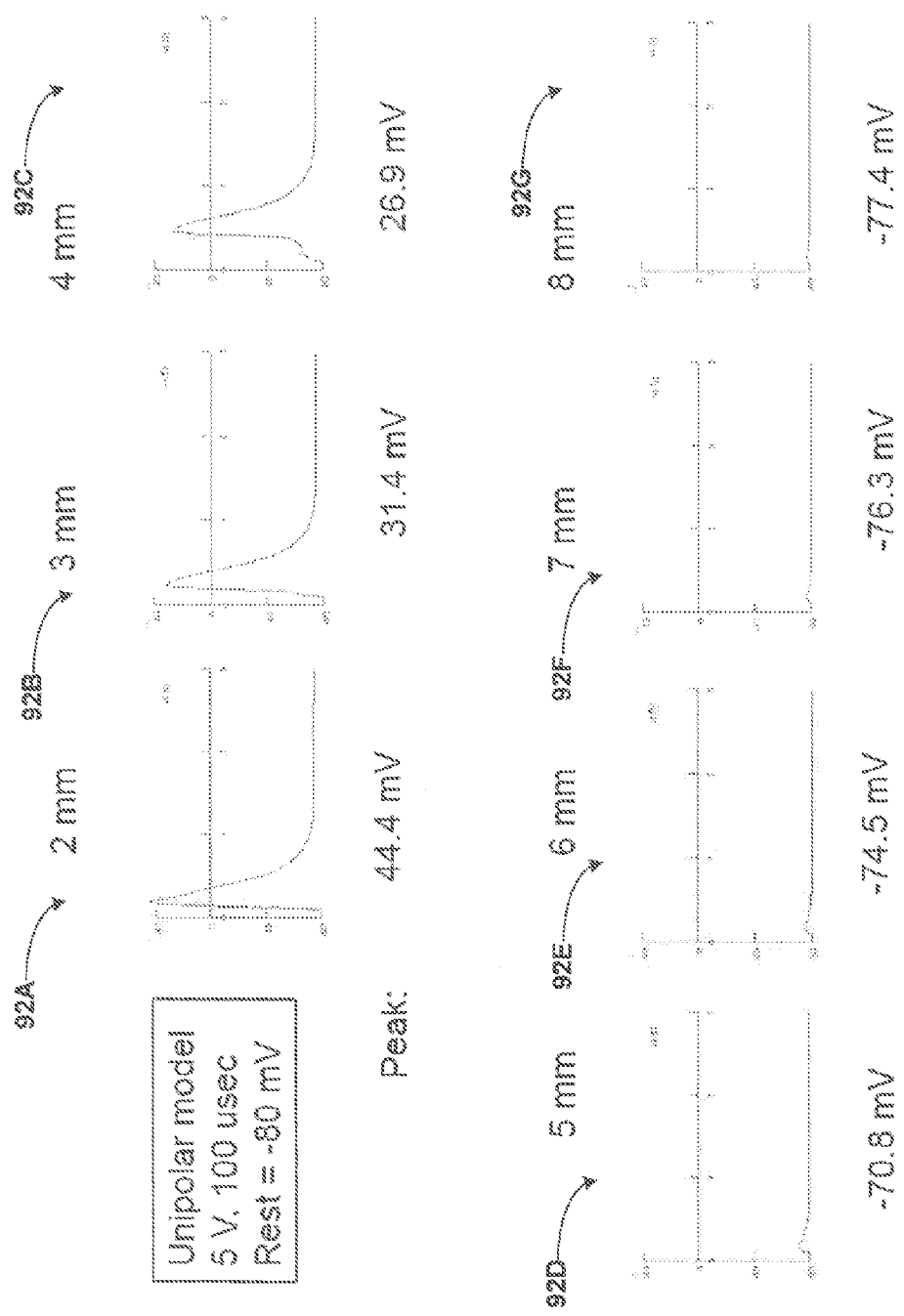
FIG. 6 is a series of plots illustrating the influence of example electrical stimulation at various distances from a stimulation electrode.

FIG. 6 is a series of plots 92A-92G illustrating the influence of example unipolar electrical stimulation as modeled at various distances (2 to 8 millimeters (mm)) from a stimulation electrode. For modeling the influence of the stimulation at each location, the stimulation electrode was assumed to have negative polarity, and the electrical stimulation was assumed to be a single pulse having an amplitude of approximately 5 volts and a pulse width of approximately 100.

To generate plots 92A-92G, the electric field generated by single-cathode unipolar stimulation was applied to single axon models at various distances away from the stimulation electrode. The transmembrane potential at rest was assumed to be approximately −80 mV, and the axonal responses to the applied electric field, as monitored in a central node of Ranvier, are shown in plots 92A-92G. As shown by FIG. 6, as distance from the stimulation electrode increases, the influence on the electrical signal on the model tissue decreases. For example, assuming an activation threshold of 0 volts, the electrical stimulation was estimated to activate neurons at 2, 3, and 4 mm from the stimulation electrode, in which case each location would be considered to be within the VTA for the electrical stimulation. This is illustrated by the fact that the plots representing 2, 3, and 4 mm each show a peak of the waveform crossing the line representing the activation threshold of 0 volts. At 5, 6, 7, and 8 millimeters, the electrical stimulation was estimated to influence the electrical activity of the neurons at each location, but did not activate the neurons, in which case each location would be considered to be within the VSTI rather than the VTA for the electrical stimulation. This is illustrated by the fact that for the plots representing 5, 6, 7 and 8 millimeters, the waveforms do not cross the line representing the activation threshold of 0 volts, although they do exhibit a smaller "peak" resulting from the stimulation. As the distance from the electrode increased, the influence of the electrical stimulation on the electrical activity of the neurons decreased.

As will be described further below, using the results from the modeling of the electrical stimulation, processor 60 may generate a graphical representation of the VTA and VSTI in relation to the stimulation electrode for display via user interface 66 of programming 14. Such a display may assist a clinician in visualizing the influence of given stimulation in terms of VTA and VSTI, e.g., when programming electrical stimulation for delivery to brain 28 of patient 12 and/or identifying a desirable implant location of one or more of electrodes 26.

In some examples, processor 60 may determine the VSTI for a given electrical stimulation as being the volume of tissue desynchronization (VTD) resulting from the electrical stimulation (80). Neurons within the VTD may be desynchronized by the delivery of electrical stimulation rather than being activated by the stimulation. To treat or manage a patient disorder, when neurons within the VTD exhibit pathological brain activity, IMD 16 may deliver electrical stimulation to a tissue site to desynchronize the neurons in a manner that eliminates or otherwise disrupts the pathological activity.

In some examples, electrical stimulation may desynchronize brain activity by changing the time at which neuronal responses are generated. This may be achieved by altering the phase response curve for a given neuron or set of neurons via the stimulation. For example, sub-threshold entrainment of neurons may cause neurons to fire more frequently with stimulation as compared to when no stimulation exists as more synaptic responses generate action potentials. In another example, activation of neurons at sub-threshold levels may cause changes in the neuronal polarization such that the normal conduction of action potentials is disrupted or abolished. For desynchronization, while the electrical stimulation does not cause neurons to fire, the electrical stimulation provides enough energy to destabilize neurons developing or exhibiting a malignant pattern of oscillation frequency.

Conversely, processor 60 may determine the VSTI for a given electrical stimulation as being the volume of tissue synchronization (VTS) resulting from the electrical stimulation (80). Neurons within the VTS may be synchronized by the delivery of electrical stimulation rather than being activated by the stimulation. For example, to treat or manage a patient disorder, IMD 16 may deliver electrical stimulation to a tissue site to synchronize one or more groups of neurons such that the neurons exhibit non-pathological brain activity. The delivered electrical stimulation may provide enough energy to influence the neurons to act together, e.g., by align the timing and phase of the electrical signals within the VTS. In some examples, the electrical stimulation may be delivered at specific phases of oscillation to influence the neurons to exhibit a particular oscillation frequency.

In some examples, electrical stimulation may synchronize neurons within the VTS by entrainment of the bioelectrical brain signals. For example, electrical stimulation delivery may synchronize brain activity within the VTS by entraining the neurons to the frequency of stimulation or a sub-frequency of stimulation in a sub-threshold fashion. The VTS may be estimated by indicating which neurons exceeded a pre-specified threshold value for polarization. Examples of entrainment of bioelectrical brain signals may include one or more of those examples described in U.S. patent application Ser. No. 13/446,801, to Wu et al., filed Apr. 13, 2012, the entire content of which is incorporated herein by reference.

In either case, the placement of electrodes 26 relative to a target tissue site within brain 28, as well as the electrical stimulation parameter values defining the electrical stimulation, may influence the ability of IMD 16 to desynchronize, synchronize, or otherwise influence brain activity in a manner that treats or manages a patient condition. Accordingly, in some examples, processor 60 may be configured to display a graphical representation of the determined VSTI (80) to a user via user interface 66, e.g., to assist the user in visualizing the VSTI resulting from the electrical stimulation. The display may assist the user in determining the desired placement of electrodes 26 and/or programming values for electrical stimulation to brain 28 of patient 12 in a manner that effectively treats or manages a patient disorder.

Figure 7:
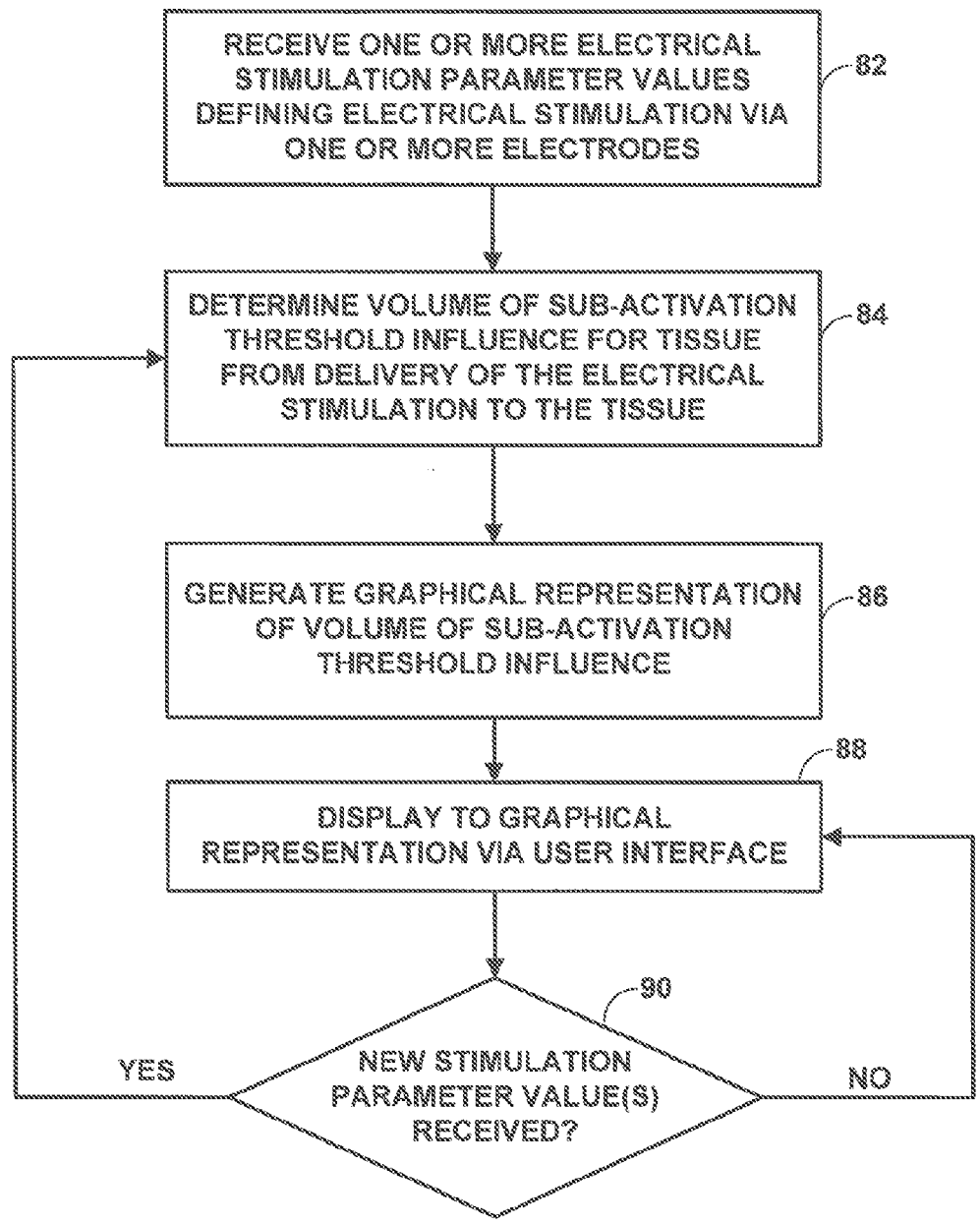
FIG. 7 is a flow diagram illustrating an example technique for displaying a VSTI.

FIG. 7 is a flow diagram illustrating an example technique for determining and displaying a VSTI to a user. Such a technique may be used by a clinician to identify desirable electrical stimulation parameter values for electrical stimulation delivered to patient 12 via one or more of electrodes 26. For example, such a technique may be used to identify electrical stimulation parameters values that result in a desired VSTI.

Similar to that described above with regard to FIG. 5, processor 60 may receive one or more electrical stimulation parameter values, e.g., from a user via user interface 66, to define an electrical stimulation therapy that may be delivered to patient 12 via one or more of electrodes 26 (82). The information received from the user via user interface 66 may further specify the location (s) of the lead and/or electrode(s) on the lead. Processor 60 may then determine the VSTI for the electrical stimulation defined by the one or more electrical stimulation parameter values and, optionally, from any other provided information such as location information (84). In some cases, the electrode/lead information may be derived from actual patient data, such as MRI, DTI, or other information obtained from the patient (e.g., in real-time during surgery) that shows the location of the electrode(s)/lead(s) relative to patient anatomy.

In view of the VSTI, processor 60 may generate a graphical representation of the VSTI (86), and then display the image to a user via a display of user interface 66 (88). In some examples, processor 60 may also determine the VTA along with the VSTI, and display a graphical representation of the VTA in combination with the VSTI. In some examples, the electrical field generated by the electrical stimulation may also be display in combination with the VSTI and/or VTA.

Figure 8:
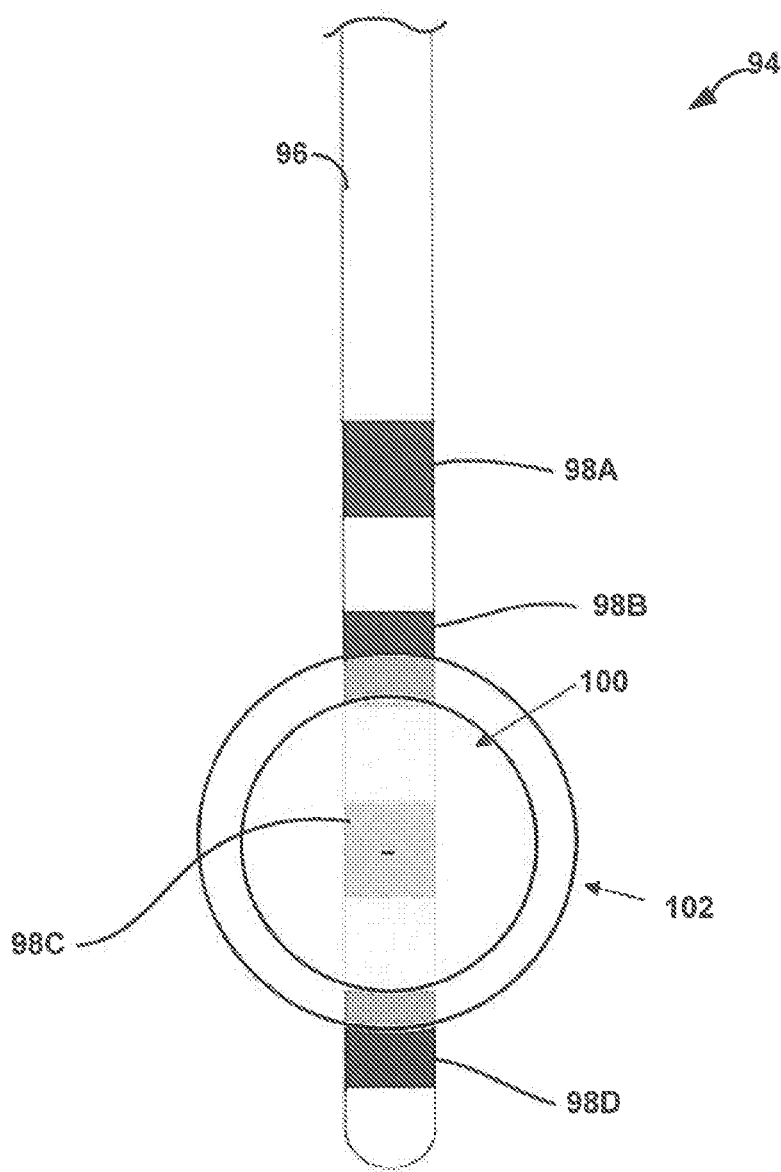
FIG. 8 is a conceptual diagram illustrating an example VSTI for electrical stimulation.

FIG. 8 is a conceptual diagram illustrating an example graphical representation 94 including VSTI 102 and VTA 100 for a given electrical stimulation. Such an image may be displayed to a user, e.g., via user interface 66 of programmer 14, using the technique of FIG. 7. In combination with VSTI 102 and VTA 100, the lead 96 is displayed with electrodes 98A-98D relative to VSTI 102 and VTA 100. As shown, graphical representation 94 indicates electrode 98C as the anode for delivering unipolar electrical stimulation (similar to that modeled in FIG. 7). VTA 100 circles electrode 98C and includes the area immediately adjacent electrode 98C. As described above, when such electrical stimulation is delivered to a tissue site, neurons of tissue within the VTA 100 may be activated by the stimulation. As shown in FIG. 7, the inner boundary of VSTI 102 is adjacent to the outer boundary of VTA 100. For neurons of tissue within VSTI 102, the electrical stimulation may influence the electrical signals but not cause the neurons to activate. In some examples, such stimulation may be used to disrupt (e.g., desynchronize or synchronize) pathological electrical activity of neurons within VSTI 102 to treat the patient condition.

In FIG. 8, the outer boundary of VSTI 102 is represented as a definite boundary. However, as the influence of the electrical stimulation may gradually decrease moving away from electrode 98C, in some examples, VSTI 102 may be represented in a manner that indicates the relative degree of influence for tissue within the VSTI 102. For example, shading may be used to illustrate VSTI 102 resulting from stimulation in which the darker the shade, the greater the degree of influence resulting from delivered electrical stimulation. Alternatively or additionally, different colors may be used to represent a greater degree of influence. For instance, warm colors may be used to represent tissues areas receiving a greater degree of influence whereas cool colors may be used to represent tissue areas receiving a lesser degree of influence. Additionally or alternatively, a definite outer boundary may be represented by defining a threshold degree of influence resulting from the stimulation. For tissue outside the boundary, the influence of the electrical stimulation may not reach the threshold degree of influenced defined by the outer boundary. Such a threshold may be defined by a user, e.g., to reflect the relative degree of stimulation found to efficiently desynchronize or synchronize neurons of a tissue site.

As noted above, graphical representation 94 may be displayed to a user via user interface 66 to assist a user in visualizing the VSTI of electrical stimulation defined by a given set of electrical stimulation parameters. In some examples, graphical representation 94 may be generated to reflect the scale of VSTI 102, VTA 100, and lead 96 relative to each other, as well as any anatomical region that may also be displayed. Although FIG. 8 illustrates a 2D image of lead 96, VSTI 102 and VTA 100, in other examples, user interface 66 may present a 3D image of lead 96, VSTI 102, and VTA 100. Likewise, while other 2D images are included in other examples of the disclosure, such images may also be presented by user interface 66 as a 3D image. Such images may also include anatomical regions that may be illustrated relative to leads, electrodes, VSTI, VTA, and the like.

Furthermore, while VSTI 102 and VTA 100 are shown as being substantially circular in shape, the shape of VSTI 102 and VTA 100 may depend on the electrical stimulation parameter values, lead and electrode characteristics, and other factors defining the electrical stimulation, as well as characteristics of tissue proximate the stimulation electrode (s). For example, the shape of VSTI 102 may depend on the stimulation vector used to deliver the electrical stimulation. In FIG. 8, for example, the stimulation vector is defined by electrode 98C along with the can or housing electrode of IMD 16. In other examples, a different shape of VSTI may result from delivering the electrical stimulation via a different vector, which may define unipolar or multipolar stimulation. The stimulation vector may include one or more of electrodes 98A-98D, a can or housing electrode of IMD 16, or other electrode(s) located on one or more other leads implanted in patient 12.

Returning to FIG. 7, after processor 60 displays graphical representation 94 via user interface 66 (88), processor 60 may receive an adjustment to one or more of the stimulation parameters values (e.g., amplitude, pulse width, frequency, and the like) used to model VSTI 102, e.g., based on user input received via user interface 66. In such an example, processor 60 may determine a new VSTI based on the electrical stimulation defined by the new electrical stimulation parameter values (84). In view of the new VSTI, processor 60 may generate a graphical representation of the VSTI (86), and then display the image to a user via a display of user interface 66 (88). Again, in some examples, processor 60 may also determine a newVTA along with the VSTI, and display a graphical representation of the VTA in combination with the VSTI.

Throughout the process, a new VSTI may be displayed alone or in combination with one or more previously displayed VSTIs, e.g., to allow a user to visualize how the VSTI changes relative to a prior VSTI based on changes to one or more stimulation parameter values. In some examples, multiple VSTIs may be determined and displayed via user interface 66 at a given time, e.g., when two or more types of electrical stimulation delivered via different stimulation electrodes (e.g., in a multi-channel system), relative to each other to allow a user to visualize the overall influence of the electrical stimulation rather than simply on a vector by vector basis.

The process of FIG. 7 may be repeated until a user has identified one or more set of stimulation parameter values that result in a desired VSTI. In some examples, when electrical stimulation parameter values are found to result in a desired VSTI, e.g., based on the VSTI influencing a particular tissue site or region or neural circuit, for a given electrode location, the parameter values may be transmitted to IMD 16 to define therapy delivered to patient 12. In this manner, a user may identify a desired set of stimulation parameter values based on the VSTI.

Figure 9:
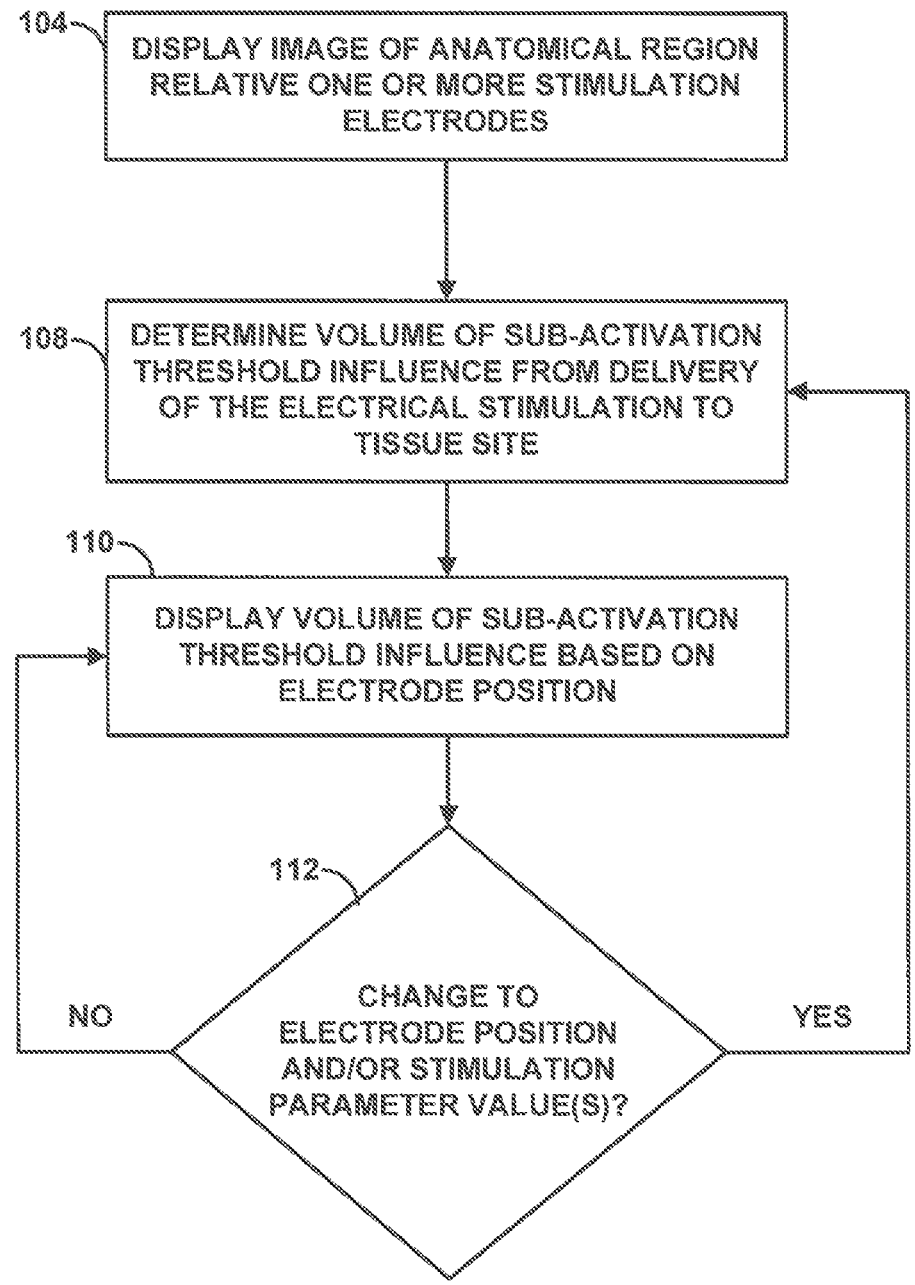
FIG. 9 is a flow diagram illustrating an example technique for displaying a VSTI.

FIG. 9 is a flow diagram illustrating an example technique for displaying a VSTI for a given stimulation relative to an image of an anatomical region. As shown, processor 60 may display an anatomical image of a tissue site (e.g., an area of potential implant in the brain of a patient) via user interface 66 relative a representation of one or more electrode(s) for delivery of electrical stimulation to a tissue site within the anatomical region (104). As in FIG. 5, the VSTI may be determined for a given set of stimulation parameter values. As the VSTI may be displayed to a user relative to the anatomical image and electrode position, a user may be assisted in visualizing the VSTI resulting from the electrical stimulation from one or more electrodes relative to the anatomical image being displayed. In some examples, processor 60 may receive changes to one or more stimulation parameter values and/or the location of one or more stimulation electrodes relative to the anatomical region (112), e.g., based on user input provided via user interface 66. In that case, processor 60 may determine (108) and display a new VSTI corresponding to the new parameter values and/or electrode location (110).

In this manner, user interface 66 may assist a user in identifying a desired location to implant one or more stimulation electrodes (such as, e.g., electrodes 26) and/or stimulation parameter values that provided for a VSTI that includes a particular anatomical region of interest. Such a process may be performed prior to or during an implant of electrodes 26 (e.g., to identify a target implant site and implant trajectory), or after electrodes 26 have been implanted (e.g., during a programming session).

By displaying an image of an anatomical region relative the VSTI for electrical stimulation, a user may be able to determine the overlap, if any, of the VSTI with known structures resulting from electrical stimulation. For DBS, processor 60 may depict a VSTI along with known anatomical circuits that include the basal ganglia, cortex locations, thalamic locations, brain stem including midbrain, and the like. As will be described further below, the presentation of an anatomical region relative to a VSTI may allow a clinician to determine if the VSTI includes target tissue sites desired to be within the VSTI or, conversely, to determine if the VSTI does not include one or more tissue sites for which it is undesirable to be within the VSTI.

Processor 60 may retrieve one or more images of anatomical regions for display stored in memory 62. Any suitable image representing an anatomical region may be used for display relative a determined VSTI. In some examples, an atlas image or other non-patient specific image of an anatomical region may be used. In other examples, a patient specific image may be used, e.g., an actual image of the anatomical region of the patient may be used (e.g., using MRI, CT, or DTI).

In other examples, a morphed atlas image may be used. A morphed atlas image may combine both an atlas image (or other non-patient specific image of an anatomical region) and an actual image of an anatomical region of the patient. A morphed atlas may allow the user to view known structures while correlating the known structures to the specific patient anatomical region.

Figure 10:
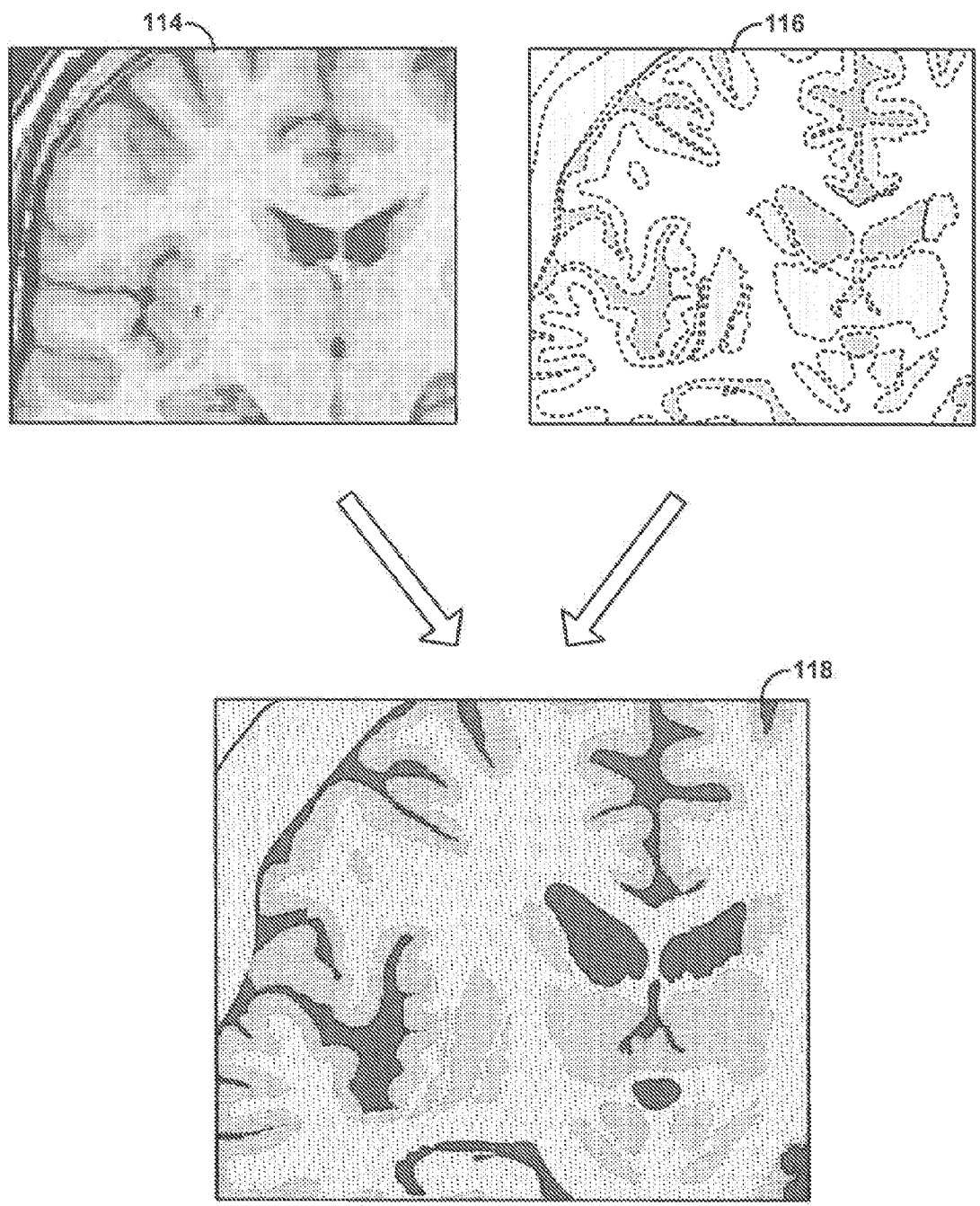
FIG. 10 is a conceptual diagram illustrating an example morphed atlas image of an anatomical region.
Figure 11:
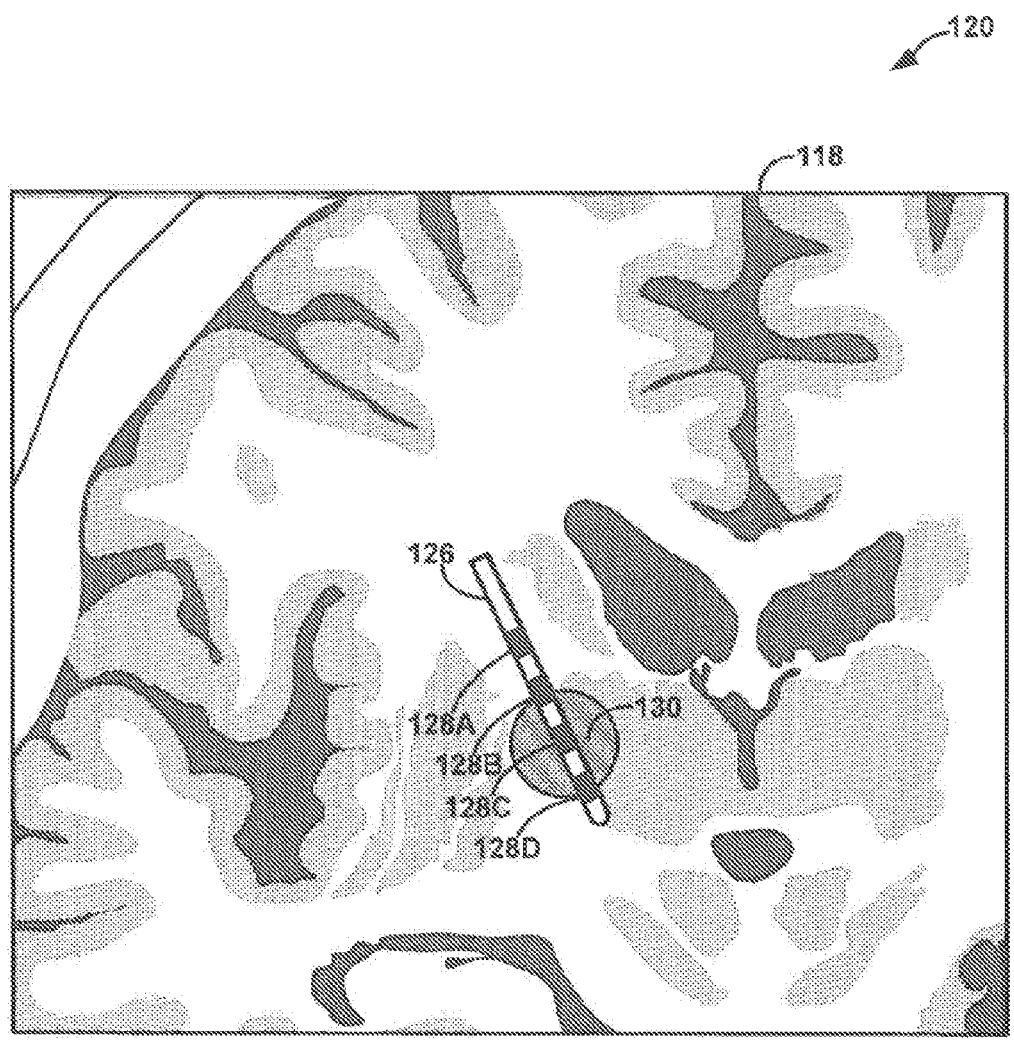
FIGS. 11-13 are conceptual diagrams illustrating various example user interface display screen shots.

FIG. 10 is a representation of morphed atlas image 118 generated from the combination of aspects of atlas image 114 and patient specific image 116. Atlas image 116 is shown as a CT image while patient specific image 116 is illustrated as a computer model. In other embodiments, atlas image 114 and patient specific image 116 may be any combination of CT images and/or computer models. As shown in FIG. 11, atlas image 114 is a reference anatomical region of a reference anatomy. Atlas image 114 is beneficial to use in programming stimulation therapy because the location of specific structures is known and readily identifiable. However, atlas image 114 is not an actual image of the anatomy of patient 12 surrounding implanted lead 14. Patient specific image 116 represents the actual anatomy of patient 12, but a clinician may not be able to easily identify the specific location of structures that should be subject to electrical stimulation.

To fit atlas image 114 to patient specific image 116, programmer 14 may essentially map the locations of structures of the atlas to the actual locations of the tissue of the patient anatomical region. This fitting may be completed by identifying specific markers common to all anatomies and fitting the remaining atlas image 114 to the coordinates of patient specific image 116. This resulting morphed atlas 118 may allow a clinician to select structures at the specific location in question. One example of how programmer 14 may create morphed atlas 118 is described in U.S. Patent Application No. 2005/0070781 by Dawant et al., entitled, ELECTROPHYSIOLOGICAL ATLAS AND APPLICATIONS OF SAME, and filed Jul. 1, 2004.

FIG. 11 is a conceptual diagram illustrating an example screen shot 120 which may be displayed by processor 60 via user interface 66. As shown, user interface 66 displays morphed atlas image 118 of FIG. 11 along with a graphical representation of lead 126 including electrodes 128A-128D displayed relative morphed atlas image. VSTI 130 is displayed for electrical stimulation delivered via electrode 128C and is shown relative to morphed atlas image 118. Screen shot 120 does not include an indication of a VTA within VSTI 130 as, e.g., the stimulation parameter values for the stimulation may not result in activation of neurons in the surrounding tissue.

Screen shot 120 may be displayed, e.g., during the example process of FIG. 10. A clinician may move the position of lead 126 and/or input one or more new stimulation parameter values, and VSTI 130 may change accordingly on the display. In this manner, a clinician may identify a desirable implant location for electrodes 128A-D and stimulation parameter values that result in VSTI 130 including a desired tissue site. As noted above, although screen 120 only includes a single lead, in other examples, multiple leads may be displayed along with multiple VSTIs resulting from electrical stimulation delivered via multiple vectors. In this manner, not only does screen 120 allow a clinician to visualize the position of a single VSTI for electrical stimulation delivered via one stimulation vector relative morphed atlas image 122, screen 120 may allow the clinician to evaluate multiple VSTIs resulting from stimulation delivered from multiple stimulation vectors relative to each other.

In some examples, such a technique may be used to identify a target implant location and/or implant trajectory for lead 20 (FIG. 1) prior to implant. Additionally or alternatively, screen 120 may be displayed in or near real time during the actual procedure to implant lead 20 within the brain of patient 12, e.g., to identify a target implant location or confirm that lead 20 is position at a previously identify implant location. In such cases, an actual image of lead 20 within an anatomical region of patient 12 may be displayed rather than a non-patient specific or morphed atlas image. During the implant procedure, a user (e.g., a clinician) may change the location of electrodes 128A-D and/or change one more stimulation parameter values to determine how the change influences VSTI 130 relative an anatomical region of patient 12. In this manner, a clinician can be visually aided by screen 120 before and during the implant procedure to facilitate the implant of lead 20. After implant of lead 20, screen 120 may assist a clinician in identifying one or more stimulation parameter values given the location of electrodes 128A-D that result in a VSTI including a desired tissue site.

In some examples, a clinician may indicate a desired VSTI 130 at a desired location relative morphed anatomical image 122 via user interface 66, and processor 60 may determine the electrode location(s) and/stimulation parameter values capable of producing the indicated VSTI 130. That is, instead of modeling VSTI 130 for a given set of electrical stimulation parameter values, a user may indicate VSTI 130 (e.g., at a given location relative to morphed anatomical image 122) to processor 60, and processor 60 may determine one or more sets of therapy parameter values that result in VSTI 130 from the delivery of the electrical stimulation. In this manner, a user may identify stimulation parameters by defining a desired VSTI rather than sequentially manipulating stimulation parameters values, e.g., in a guess and check fashion, to arrive at the desired VSTI.

In some examples, VSTI 130 may result from electrical stimulation defined according to more than one set of therapy parameter values. For example, two different therapy programs including different values for at least one therapy parameter may define electrical stimulation that result in substantially the same VSTI. In such cases, processor 60 may be configured to determine multiple different therapy programs that result in substantially the same VSTI. Processor 60 may present the different options to a clinician via user interface 66 for review. In some examples, processor 60 may be configured to list the various options according to one or more evaluation parameters. For example, processor 60 may present the various options via user interface 66 according to power consumption associated with each of the stimulation options. A user may select one or more of the stimulation options resulting in the desired VSTI, and then processor 60 may transmit the selected stimulation option(s) to IMD 16 for use defining the therapy delivered to patient 12.

Conversely, in some examples, substantially the same stimulation parameter values may result in different VSTIs, e.g., based on anatomical implant location of the stimulation electrodes and/or patient-specific characteristics associated with the target tissue. Accordingly, in some examples, processor 60 may be configured to determine and display via user interface 66 multiple VSTIs resulting from the delivery of electrical stimulation according to substantially the same stimulation parameter values. In this manner, a user may be able to evaluate the various stimulation locations in terms of comparative sizes of the VSTIs yielded by substantially the same parameter sets at each of the different stimulation locations.

The stimulation parameters resulting from a desired target VSTI may be determined using a variety of approaches, as discussed above. In one case, one or more processors of the system may use different stimulation parameter sets, electrode information (e.g., configuration, polarity, and so on), and/or tissue data, for example, to derive multiple VSTIs. These derived VSTIs may then be compared to the target VSTI to determine which of the multiple derived VSTIs best approximates the target VSTI. Then, if desired, the parameters associated with the derived VSTI that is the "best fit" may be changed slightly to even more closely achieve the VSTI that matches the target. This process may be repeated any number of times to obtain a derived VSTI that substantially matches the desired VSTI. The parameter values used to obtain this derived VSTI may then be used to select the electrode location and/or program the IMD.

In one example, equations or lookup tables may be developed to directly match a desired target VSTI to one or more parameter sets that may specify both stimulation parameters as well as electrode and location information in one example. A user may provide, as input, a description of the desired VSTI. Using these equations or lookup tables, the system may suggest one or more parameter sets that will achieve this target VSTI. The user may select the option that best matches other therapy and system objectives (e.g., power saving, patient-specific therapy needs, and so on.) Such a system may even be customized according to patient-specific information that may take into account data derived from MRI, CT, DTI, and other diagnostic and analytical tools.

Figure 12:
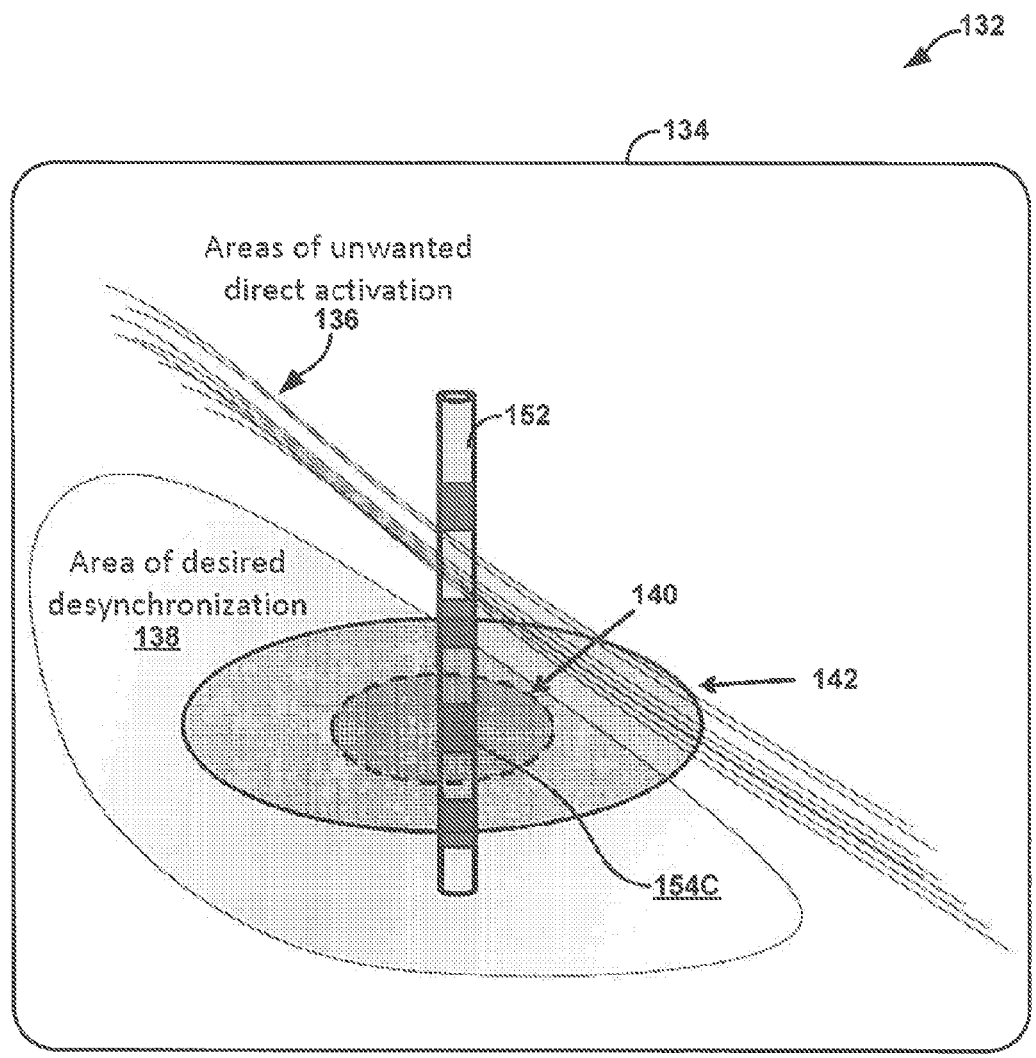

FIG. 12 is a conceptual diagram illustrating an example screen shot 132 that may be displayed via user interface 66. Screen shot 132 includes an image showing VTA 140 and VSTI 142 relative lead 152 including four electrodes. As shown, lead 152, electrode 154C, VTA 140, and VSTI 142 are all displayed relative image 134. Image 134 includes an indicator indicating a generic anatomical area of desired desynchronization (138) (e.g., an area in which desynchronization has been found to treat a patient disorder by disrupting pathological activity) as well as a generic anatomical area of unwanted direct activation (e.g., an area in which it is undesirable to activate neurons via electrical stimulation). As shown in FIG. 12, electrode 154C of lead 152 is located such that, for the selected set of stimulation parameter values, VTA 140 resulting from the stimulation does not include a portion of the area of undesired activation but VSTI 142 resulting from the stimulation does include a portion of the area of desired desynchronization.

A clinician could arrive at such a configuration using one or more of the techniques described herein using user interface 66 of programmer 14. For example, using the technique of FIG. 9, after a clinician determines that a particular lead location and/or set of stimulation therapy parameter values results in a VTA including a portion of the area of unwanted activation and/or a VSTI that does not include a portion of the area of desired desynchronization, the clinician may modify the location of lead 152 and/or modify one or more stimulation parameter values to determine a combination of lead location and stimulation therapy parameter values that provide for the relationship shown in FIG. 12.

Figure 13:
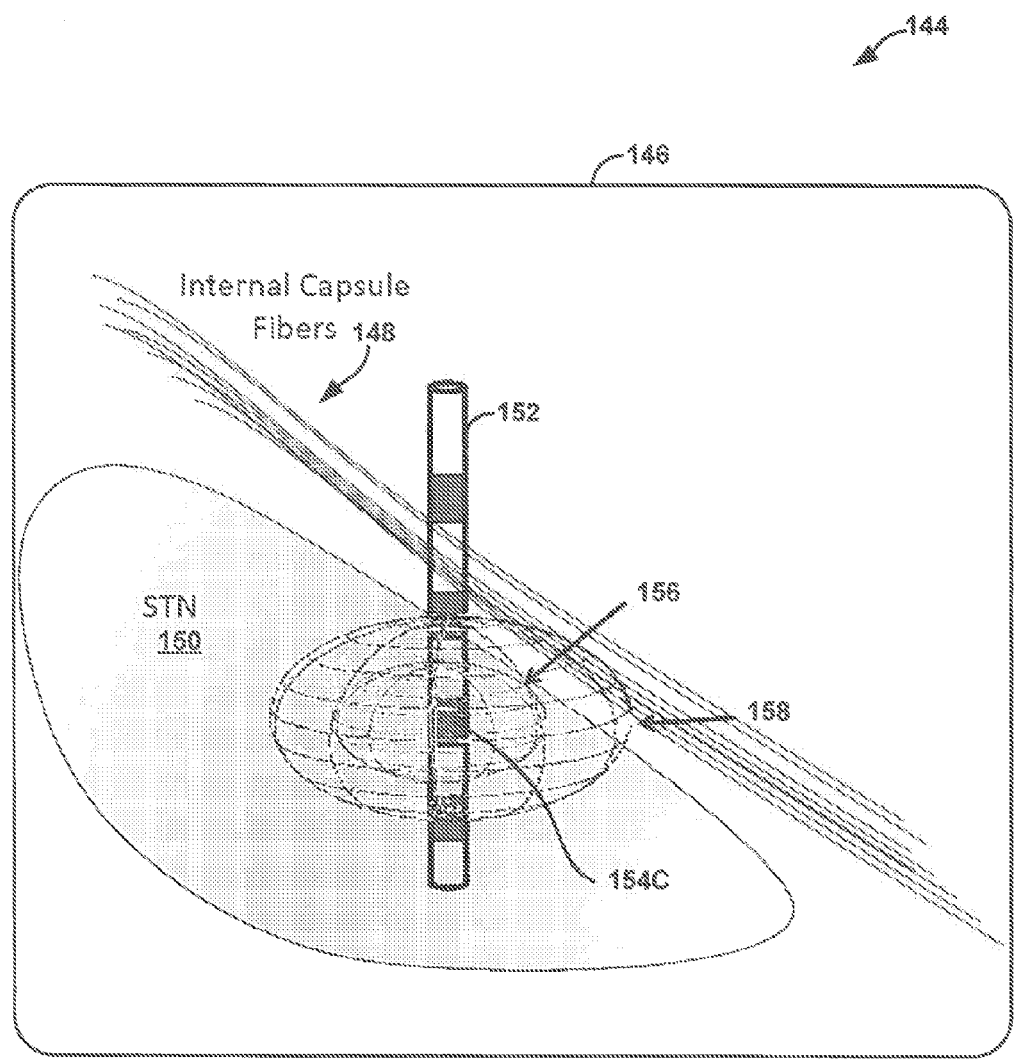

FIG. 13 is another conceptual diagram illustrating an example screen shot 144 that may be displayed via user interface 66. Screen shot 144 includes an image showing VTA 156 and VSTI 158 relative lead 152 including four electrodes. As shown, lead 152, electrode 154C, VTA 156, and VSTI 158 are all displayed relative image 146. Unlike that of FIG. 13, image 146 includes representation of specific anatomical sites of patient 12 relative VTA 156 and VSTI 158. In particular, VTA 156 and VSTI 158 are display relative to the anatomical regions of STN 150 and internal capsule fibers 148. Unlike that of FIG. 13, VTA 156 and VSTI 158 are indicated by 3D representations.

Again, the display of FIG. 13 may facilitate a clinician in the position of lead 152 and/or programming of electrical stimulation to patient 12 via IMD 16. In the case of STN 150 being an area of desired desynchronization (e.g., an area in which desynchronization has been found to treat a patient disorder by disrupting pathological activity) and internal capsule fibers 148 being an area of unwanted direct activation (e.g., an area in which it is undesired to activate neurons via electrical stimulation), screen shot 144 may be used by a clinician to identify the location of electrodes and/or stimulation parameter values that result in VSTI 158 overlaying a portion of STN 150 and VTA 156 not overlying a portion of internal capsule fibers 148. A clinician could arrive at such a configuration using, e.g., the process of FIG. 9 guided by user interface 66 of programmer 14.

As described above, examples of the disclosure may provide for one or more advantages. In some examples, VSTI may be used as a tool for automating or visualizing the brain targeting and programming of DBS in a clinical setting. In some examples, VSTI may be depicted within a neural circuit that is pathological (e.g., to display electrical activity associated with the presence of one or more patient disorders). The delivery of electrical stimulation in the form of sub-activation threshold stimulation to desynchronize or synchronize the electrical signals may be used to change bioelectrical signals in the neural circuit from a pathological state to a non-pathological state (e.g., electrical activity not associated with a patient disorder). The volume of tissue and specific tissues directly desynchronized (or synchronized) for a given electrical stimulation may be shown to a physician as a surgical planning tool and prior to surgical implantation. Potential DBS lead trajectories may also be displayed. Potential locations of a VSTI can be depicted and used to facilitate implantation and programming as well as demonstrate the use of DBS therapy to a patient.

In some examples, a VSTI may be displayed relative to one or more neuronal characteristics (e.g., fiber diameter or fiber direction). VSTI may be represented locally (volumes of tissue immediately adjacent to stimulating electrodes) or may be traced through known networks of brain connectivity. For example, causing desynchronized activity in a given fiber bundle may propagate to distant structures to which that bundle is connected in either an inhibitory or excitatory fashion. This could be from deep structures to cortical structures, between separated deep structures, or even on a gross scale (hemisphere to hemisphere). In such cases, the VSTI may be displayed to encompass all structures influenced by the subthreshold stimulation even though not proximate the stimulation electrode.

In some examples, in therapy systems with multiple stimulation capability (many leads, interleaved programs, and the like), representations of VSTIs may be visualized in the same context to allow compound or overlapping effects to be noted. For example, several areas of partial desynchronization may yield more complete desynchronization in areas of overlap.

In some examples, therapy system 10 may provide synchronization based guidance for lead implant, stimulation location or parameter selection. This might be an anatomical region that, when desynchronized in the past in this patient or in other representative patients, yielded a given effect or side effect. System 10 may display this guidance visually via user interface 66 such that the user may attempt to achieve the result via manual adjustment of location or parameters, or the system may propose or automate locations or parameter sets that cause predicted VSTIs to cover the regions in which synchrony changes are desired.

The techniques described in this disclosure may be implemented, at least in part, in hardware, software, firmware or any combination thereof. For example, various aspects of the techniques may be implemented within one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems and devices described in this disclosure may be embodied as instructions on a computer-readable medium such as RAM, ROM, NVRAM, EEPROM, FLASH memory, magnetic media, optical media, or the like. The instructions may be executed to support one or more aspects of the functionality described in this disclosure.

If implemented in software, the techniques described in this disclosure may be stored on or transmitted over as one or more instructions or code on a non-transitory computer-readable medium. Computer-readable media may include non-transitory computer storage media or communication media including any medium that facilitates transfer of a computer program from one place to another. Data storage media may be any available media that can be accessed by one or more computers or one or more processors to retrieve instructions, code and/or data structures for implementation of the techniques described in this disclosure. By way of example, and not limitation, such data storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

The code may be executed by one or more processors, such as one or more digital signal processors (DSPs), general purpose microprocessors, application specific integrated circuits (ASICs), field programmable logic arrays (FPGAs), state machines or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

In addition, it should be noted that the systems described herein may not be limited to treatment of a human patient. In alternative examples, these systems may be implemented in non-human patients, e.g., primates, canines, equines, pigs, and felines. These animals may undergo clinical or research therapies that my benefit from the subject matter of this disclosure.

Various examples of the disclosure have been described. These and other examples are within the scope of the following claims.

The invention claimed is:

1. A method comprising:
receiving at least one electrical stimulation parameter value defining electrical stimulation for delivery via one or more electrodes to a tissue site; and
determining, via one or more processors, a volume of sub-activation threshold impact from the delivery of the electrical stimulation to the tissue site, wherein the volume of sub-activation threshold impact is defined by a volume of tissue electrically influenced by the electrical stimulation but in which neurons are not directly activated by the electrical stimulation.

2. The method of claim 1, further comprising displaying a representation of the determined volume of sub-activation threshold impact via a user interface.

3. The method of claim 2, further comprising displaying an image of an anatomical region relative to the representation of the determined volume of sub-activation threshold impact via the user interface.

4. The method of claim 2, further comprising displaying a representation of the one or more electrodes relative to the representation of the determined volume of sub-activation threshold impact via the user interface.

5. The method of claim 2, further comprising displaying an image of an anatomical region and the one or more electrodes relative to the representation of the determined volume of sub-activation threshold impact via the user interface.

6. The method of claim 5, further comprising:
receiving user input modifying a position of one or more of the electrodes relative to the image of the anatomical region; and
repositioning the representation of the determined volume of sub-activation threshold impact relative the anatomical image based on the modified position of the one or more electrodes.

7. The method of claim 2, further comprising:
determining, via the one or more processors, a volume of tissue activation from the delivery of the electrical stimulation to the tissue site; and
displaying a representation of the determined volume of tissue activation in combination with the representation of the determined volume of tissue sub-activation threshold impact via the user interface.

8. The method of claim 1, wherein the volume of sub-activation threshold impact comprises a first volume of sub-activation threshold impact, the method further comprising:
receiving a modification to one or more of the at least one electrical stimulation parameter value defining the electrical stimulation or the one or more electrodes; and
determining, via one or more processors, a second volume of sub-activation threshold impact for tissue from the delivery of the modified electrical stimulation to the tissue site.

9. The method of claim 8, further comprising displaying, via a user interface, a representation of the first volume of sub-activation threshold impact and the modified volume of sub-activation threshold impact.

10. The method of claim 1, wherein determining, via one or more processors, the volume of sub-activation threshold impact for tissue from the delivery of the electrical stimulation to the tissue site comprises:
delivering the electrical stimulation to the tissue site;
sensing electrical signals via one or more electrodes in conjunction with the delivery of electrical stimulation to the tissue site at one or more locations; and
determining the volume of sub-activation threshold impact for tissue from the delivery of the electrical stimulation to the tissue site based on the sensed electrical signals.

11. The method of claim 1, further comprising:
receiving an indication of a target volume of sub-activation threshold impact for tissue; and
determining one or more electrical stimulation parameter values for electrical stimulation for delivery via the one or more electrodes to result in the target volume of volume of sub-activation threshold impact.

12. A system comprising one or more processors configured to receive at least one electrical stimulation parameter value defining electrical stimulation for delivery via one or more electrodes to a tissue site, and determine a volume of sub-activation threshold impact from the delivery of the electrical stimulation to the tissue site, wherein the volume of sub-activation threshold impact is defined by a volume of tissue electrically influenced by the electrical stimulation but in which neurons are not directly activated by the electrical stimulation.

13. The system of claim 12, further comprising a user interface configured to display a representation of the determined volume of sub-activation threshold impact.

14. The system of claim 13, wherein the user interface is configured to display an image of an anatomical region relative to the representation of the determined volume of sub-activation threshold impact.

15. The system of claim 13, wherein the user interface is configured to display a representation of the one or more electrodes relative the representation of the determined volume of sub-activation threshold impact.

16. The system of claim 13, wherein the user interface is configured to display an image of an anatomical region and an image of the one or more electrodes relative the representation of the determined volume of sub-activation threshold impact.

17. The system of claim 16, wherein the one or more processors are configured to receive user input modifying a position of an image of one or more of the electrodes relative to the image of the anatomical region displayed by the user interface, and based on the user input, to reposition the representation of the determined volume of sub-activation threshold impact relative to the anatomical image displayed by the user interface.

18. The system of claim 13, wherein the one or more processors are configured to determine a volume of tissue activation from the delivery of the electrical stimulation to the tissue site, and wherein the user interface is configured to display a representation of the determined volume of tissue activation in combination with the representation of the determined volume of tissue sub-activation threshold impact via the user interface.

19. The system of claim 12, wherein the volume of sub-activation threshold impact comprises a first volume of sub-activation threshold impact, wherein the one or more processors are configured to receive a modification to one or more of the at least one electrical stimulation parameter value defining electrical stimulation or the one or more electrodes, and determine a second volume of sub-activation threshold impact for tissue from the delivery of the modified electrical stimulation to the tissue site.

20. The system of claim 19, further comprising a user interface configured to display a representation of the first volume of sub-activation threshold impact and the modified volume of sub-activation threshold impact.

21. The system of claim 12, wherein the one or more processors are configured to control the delivery of the electrical stimulation to the tissue site, sense electrical signals via one or more electrodes in conjunction with the delivery of electrical stimulation to the tissue site at one or more locations, and determine the volume of sub-activation threshold impact for tissue from the delivery of the electrical stimulation to the tissue site based on the sensed electrical signals.

22. The system of claim 12, wherein the one or more processors are configured to receive an indication of a target volume of sub-activation threshold impact for tissue, and determine one or more electrical stimulation parameter value for electrical stimulation for delivery via the one or more electrodes to result in the target volume of sub-activation threshold impact.

23. A system comprising:
means for receiving at least one electrical stimulation parameter value defining electrical stimulation for delivery via one or more electrodes to a tissue site; and
means for determining a volume of sub-activation threshold impact from the delivery of the electrical stimulation to the tissue site, wherein the volume of sub-activation threshold impact is defined by a volume of tissue electrically influenced by the electrical stimulation but in which neurons are not directly activated by the electrical stimulation.

24. A non-transitory computer-readable storage medium including instructions to cause one or more processors to:
receive at least one electrical stimulation parameter value defining electrical stimulation for delivery via one or more electrodes to a tissue site; and
determine a volume of sub-activation threshold impact from the delivery of the electrical stimulation to the tissue site, wherein the volume of sub-activation threshold impact is defined by a volume of tissue electrically influenced by the electrical stimulation but in which neurons are not directly activated by the electrical stimulation.

25. A system comprising one or more processors configured to receive an indication of a target volume of sub-activation threshold impact for tissue, and determine one or more electrical stimulation parameter values for electrical stimulation for delivery via the one or more electrodes to result in the target volume of sub-activation threshold impact, wherein the volume of sub-activation threshold impact is defined by a volume of tissue electrically influenced by the electrical stimulation but in which neurons are not directly activated by the electrical stimulation.

* * * * *